(12) United States Patent
Tawil

(10) Patent No.: US 8,165,894 B2
(45) Date of Patent: Apr. 24, 2012

(54) FULLY AUTOMATED HEALTH PLAN ADMINISTRATOR

(76) Inventor: Jack J. Tawil, Merritt Island, FL (US)

( * ) Notice: Subject to any disclaimer, the term of this patent is extended or adjusted under 35 U.S.C. 154(b) by 1348 days.

(21) Appl. No.: 11/738,099

(22) Filed: Apr. 20, 2007

(65) Prior Publication Data

US 2007/0250352 A1 Oct. 25, 2007

Related U.S. Application Data

(60) Provisional application No. 60/793,669, filed on Apr. 20, 2006.

(51) Int. Cl.
*G06Q 10/00* (2006.01)
*G06Q 50/00* (2006.01)
*G06Q 40/00* (2012.01)

(52) U.S. Cl. ................................. 705/2; 705/3; 705/4

(58) Field of Classification Search ............... 705/2–4
See application file for complete search history.

(56) References Cited

U.S. PATENT DOCUMENTS

| | | | |
|---|---|---|---|
| 5,018,067 A * | 5/1991 | Mohlenbrock et al. | 600/300 |
| 5,225,976 A | 7/1993 | Tawil | |
| 5,519,607 A | 5/1996 | Tawil | |
| 5,519,707 A | 5/1996 | Subramanian et al. | |
| 5,845,254 A | 12/1998 | Lockwood et al. | |
| 6,151,581 A * | 11/2000 | Kraftson et al. | 705/3 |
| 2004/0242972 A1 * | 12/2004 | Adak et al. | 600/300 |
| 2006/0161456 A1 * | 7/2006 | Baker et al. | 705/2 |

FOREIGN PATENT DOCUMENTS

EP 297780 A2 * 1/1989

OTHER PUBLICATIONS

Szilagya, Peter G. "Managed care for children: Effect on access to care and utilization of health services." Children and Managed Health Care, 1998, vol. 8 (2). pp. 39-59.*

* cited by examiner

*Primary Examiner* — Sheetal R Rangrej

(57) ABSTRACT

A system for fully automating the administration of a health plan. The system accepts inputs from enrollees, insureds, providers, insurers and vendors, but requires no physical data entry from the plan administrator. The system also features an automated methodology that measures patient treatment outcomes in terms of quality-adjusted life-years, by diagnosis and by medical treatment provider. The system also includes automated methods for: a "just-in-time" appointment scheduler, an editable archive of prototypical treatment plans, measuring the diagnostic accuracy of diagnostic physicians and for measuring the complication rate of treatment providers.

34 Claims, 17 Drawing Sheets

The DOCTOR SHOPPER<sup>SM</sup>

(Notes on Page Two)

YOUR DIAGNOSIS IS: 550.90 Repair, Initial, Inguinal Hernia, Reducible

RECOMMENDED DOCTOR: _____P.T. Graph_____

| REFERRAL SATISFACTION INDEX | |
|---|---|
| Dr. Harvey M. Greene | 86.3 |
| Average, All Diagnosticians | 84.2 |

PRICES                                                                 DOCTORS

| CPT | DESCRIPTION | QTY | BENEFIT | Aaron | Bosch | Cordell | Graph | Haines | Oscar | Thurgood | Williams |
|---|---|---|---|---|---|---|---|---|---|---|---|
| 90060 | Office Visit, Intermed. | 3 | $ 135 | $ 135V | $ 120 | $ 150 | $ 135 | $ 90 | $ 165 | $ 150 | $ 120 |
| 49505 | Repair, initial, Inguinal Hernia | 1 | $ 1,015 | $ 925V | $ 795 | $ 1,275 | $ 995 | $ 480# | $ 875 | $ 1,495 | $ 725 |
| | TOTALS: | | $ 1,250 | $ 1,060V | $ 915 | $ 1,425 | $ 1,130 | $ 570 | $ 1,040 | $ 1,645 | $ 845 |
| GUARANTEED PRICES — EXPIRE ON: | | | | | | | 9/15/97 | 11/30/97 | | | |
| HOSPITAL 1 (see page 2 for hospital names) | | $ | 2,550 | $ 2,200 | $ 4,950 | $ 3,200 | $ 2,200 | $ 1,700 | $ | $ 4,950 | $ 2,150 |
| Other Doctors | | $ | 360 | $ 350 | $ 450 | $ 350 | $ 350 | $ 360 | $ | $ 450 | $ 335 |
| HOSPITAL 2 (see page 2 for hospital names) | | $ | 2,550 | $ 3,200 | $ 2,150 | $ 2,200 | $ 2,500 | $ 2,200 | $ | $ 2,150 | $ 2,500 |
| Other Doctors | | $ | 360 | $ 350 | $ 335 | $ 350 | $ 350 | $ 350 | $ | $ 335 | $ 355 |
| BUNDLED PRICE DISCOUNT (Package Deal) | | | | | | | | | | | |
| with Hospital 1 | | $ | | $ 150 | $ 0 | $ 140 | $ 150 | $ 0 | $ | $ 175 | $ 0 |
| with Hospital 2 | | $ | | $ 375 | $ 0 | $ 75 | $ 200 | $ 0 | $ | $ 50 | $ 0 |

NET TO INSURED (Doctors + Hospital)

| | | Aaron | Bosch | Cordell | Graph | Haines | Oscar | Thurgood | Williams |
|---|---|---|---|---|---|---|---|---|---|
| With Hospital 1 | Individual Prices | $ 550 | $ -2,155 | $ -815 | $ 480 | $ 1,530 | $ | $ -2,885 | $ 830 |
| | Bundled Price | $ 700 | $ -2,155 | $ -675 | $ 630 | $ 1,530 | $ | $ -2,710 | $ 830 |
| With Hospital 2 | Individual Prices | $ -450 | $ 760 | $ 185 | $ 180 | $ 1,040 | $ | $ 30 | $ 460 |
| | Bundled Price | $ -75 | $ 760 | $ 260 | $ 380 | $ 1,040 | $ | $ 80 | $ 460 |

PERFORMANCE

The R-E-MEDI system provides three measures of a doctor's performance: 1) The Outcomes Index indicates how well patients with your diagnosis and prognosis rating have recovered under that doctor's care (100 is perfect); 2) the Patient Satisfaction Index measures the overall satisfaction of a doctor's patients (100 is perfect); and 3) the Nurses Index is the number of different nurses and their family members that a doctor has treated in the past 12 months. For more information on what the Outcomes Index means with regard to your diagnosis, please see the receptionist.

| | Community Average | Aaron | Bosch | Cordell | Graph | Haines | Oscar | Thurgood | Williams |
|---|---|---|---|---|---|---|---|---|---|
| Outcomes Index (Prog. Rating = 8) | 72 | | | | | | | | |
| with Hospital 1 | 69 | 79 | 82 | 78 | 68 | | | 83 | 76 |
| with Hospital 2 | 72 | 72 | 70 | 77 | 71 | | | 80 | 75 |
| Patient Satisfaction Index | 87 | 87 | 90 | 93 | 94 | 81 | | 95 | 85 |
| Nurses Index | 6 | 3 | 3 | 9 | 10 | 0 | | 19 | 6 |

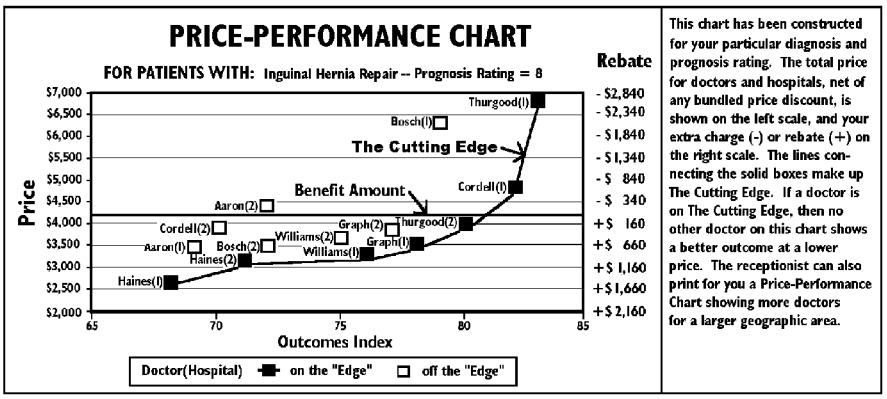

This chart has been constructed for your particular diagnosis and prognosis rating. The total price for doctors and hospitals, net of any bundled price discount, is shown on the left scale, and your extra charge (-) or rebate (+) on the right scale. The lines connecting the solid boxes make up The Cutting Edge. If a doctor is on The Cutting Edge, then no other doctor on this chart shows a better outcome at a lower price. The receptionist can also print for you a Price-Performance Chart showing more doctors for a larger geographic area.

\*\*\* ALL DATA ARE HYPOTHETICAL \*\*\*                © Copyright 1994-2005 Research Enterprises, Inc.

*FIG. 16*

The DOCTOR SHOPPER℠
CREDENTIALS

| Doctor | Age Sex | Medical Specialty[1] | Yrs In Prac- tice | Medical School Name/Degree/Rank[2] | Class[3] Rank/Size | Residency | Malpractice Suits[4] Lost Settled | | Affiliations Hospital 1 Hospital 2 | University | Other[5] |
|---|---|---|---|---|---|---|---|---|---|---|---|
| Aaron, GM | M46 | +Gen. Surgery | 14 | U of Chicago /MD/ 6 | 62/ 87 | VA Mason | 2 | 3 | Mercy Westview Comm. | -- | MC MA A |
| Bosch, RL | M45 | +Gen. Surgery | 16 | U of WA /MD/ 30 | 23/ 76 | Mt. Sinai NYC | 2 | 4 | University Metropolitan | -- | MC MA |
| Cordell, TF | F41 | +Gen. Surgery | 10 | Indiana U /MD/ 54 | 32/ 54 | Deaconess, Spok | | 3 | Westview Comm. Mercy | -- | MC A |
| Graph, PT | M52 | +Gen. Surgery | 16 | J Hopkins /MD/ 22 | 10/ 22 | Veterans SDiego | 1 | 1 | Mercy St. Mary's | State U | A |
| Haines, JM | M33 | +Gen. Surgery | 1 | PA S U /MD/ 19 | 12/ 19 | VA Mason | 0 | 1 | State General Mercy | -- | MC A NI |
| Oscar, OM Thurgood, TC | M64 | +Gen. Surgery | 21 | Harvard *Montreal* /MD/ 1 | 18/ 45 | MA General | 0 | 1 | University Metropolitan | State U | MC P A |
| Williams, RD | F38 | +Gen. Surgery | 8 | U of MD /MD/ 58 | 8/ 28 | Balt Co | 1 | 4 | Metropolitan St. Mary's | -- | MC MA |

OFFICE ADDRESS/CREDIT CARDS
1. GM Aaron, 1622 24th Ave. 684-7632 MC, V, AX
2. RL Bosch, 1959 NE Pacific St., 548-4921 MC, V, DS
3. TF Cordell, 1832 NE Pacific St., 548-6896 MC, V
4. PT Graph, 3427 NE 45th St., 525-1379 MC, V
5. JM Haines, 164 E Galer St., 684-4715 MC, V, AX
6. OM Oscar, 3211 E Madison St., 323-4932 MC, V, N
7. TC Thurgood, 480 Pacific St., 632-4513 MC, V
8. RD Williams, 2379 4th Ave., 684-0811 MC, V

**NOTES TO *The DOCTOR SHOPPER***

Page 1
  *#* denotes that the doctor may have performed the procedure fewer than 15 times.
  *√* indicates that doctor's price varies from patient to patient.

1. *+/-* denotes the doctor (is/is not) board certified in specialty.
2. School Rank: As reported in Gourman (*Gourman Report: A Rating of Graduate and Professional Programs in American and International Universities*, 5th ed., NES 1988); 125 U.S., 16 Canadian, and 86 foreign (excl. Canada) medical schools are ranked; *italics* identify foreign medical schools.
3. Class Rank/Size: Reports the doctor's academic ranking within his graduating class; for example, 5/25 means that the doctor ranked 5th in a graduating class of 25 students.
4. Malpractice Suits: Number of suits lost and settled within the past 3 years; but the reported number may apply to fewer than 3 years for a newer practice.
5. Other: MC = accepts Medicare patients; MA = accepts Medicaid patients; NP = new practice w/aggressive pricing; P = Personal Health Care Manager; A = patient's share of treatment cost is payable at time of treatment.

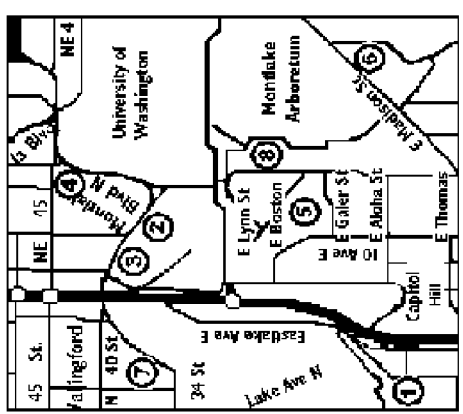

FIG. 17

FULLY AUTOMATED HEALTH PLAN ADMINISTRATOR

CROSS-REFERENCE TO RELATED APPLICATIONS

This application claims the benefit of U.S. Provisional Application No. 60/793,669, filed Apr. 20, 2006, which is incorporated herein by reference.

BACKGROUND OF THE INVENTION

Health care costs have resumed their rise at double-digit rates—after moderating in the early 1990's as managed care became widespread. The 2006 Towers Perrin Health Care Cost Survey reports that gross health care expenditures in the U.S. have increased by 140% over the past 10 years. This report can be found on-line at URL: http://www.towersperrin.com/tp/getwebcachedoc?webc=HRS/USA/2006/200605/li-nk.pdf.

Administrative costs represent a significant share of the $1.7 trillion that the U.S. currently is spending per year on health care. In a speech in March, 2006, Uwe Reinhardt, James Madison Professor of Political Economy at Princeton University, told a capacity crowd that the U.S. is spending $300 billion per year on health care administrative costs; an amount he believes could be sliced in half without affecting health outcomes [http://www.dukenews.duke.edu/2006/03/healthcosts.html].

Although many of the nation's providers have converted from paper to electronic records, much ground remains to be covered. Unfortunately, the rate at which systems are currently being converted is insufficient to materially offset the double-digit annual rate increases in health care costs. The present invention not only promotes the use of electronic records, but it also provides a method whereby, for the first time, a health care plan administrator can operate a health care plan in a fully automated mode, requiring neither the manual input of data or information, nor the manual review of claims. The present invention accepts on-line inputs from patients, physicians, other providers, an insurer and outside vendors, then processes the information and makes it available to those authorized to access it via an integrated and automated administrator.

In addition to controlling escalating health care costs, the ability to measure accurately health care quality—especially patient outcomes—has also been elusive. While the health care quality of entire facilities (e.g., hospitals, health plans) has been compared, little progress has been made with respect to comparing the performance of individual providers.

While some quality measurement systems, such as HEDIS [www.ncqa.org/programs/hedis/], compare compliance (e.g., the percentage of a providers' patients receiving vaccinations), none has been successful in providing a method for comparing the outcomes of individual providers. A persistent problem has been the difficulty in making comparisons of provider outcomes when patients initially face dissimilar recovery risks, due to illness severity, co-morbidities and other risk factors.

Accordingly methods and systems for fully automated health plan administration, including methods for making valid comparisons of provider outcomes, are needed.

SUMMARY OF THE INVENTION

Although the preferred specification primarily references "illnesses" and "injuries", as well as "treatments" and "procedures", this patent applies more generally to any transaction in which a patient seeks to receive a benefit covered by that patient's benefit plan.

One aspect of the present invention provides a fully automated and integrated health care plan administrator. It performs all of the key functions that are necessary to operate a health plan by utilizing databases and processing means for: enrolling and removing insureds and providers from the health plan; establishing benefit amounts for each covered benefit; validating real-time the insureds' eligibility to receive benefits under the plan; processing health benefit claims that result when an insured seeks medical services; maintaining an electronic medical record (EMR) system; reconciling the monetary accounts of the insurer, providers and insureds; disbursing funds to insureds, physicians and other providers; evaluating health care records to detect fraud; billing of patients; and updating any databases to reflect changes resulting from these and other transactions.

Additional aspects of the present invention include some valuable functions that are not essential for operating a health plan, but which also can be automated. These include an archive of editable treatment plan prototypes, patient-administered surveys for assessing provider quality; an apparatus and method for measuring and comparing risk-adjusted patient outcomes, a method for measuring the accuracy and timeliness of diagnoses, a method for measuring the complication rate of providers, and a "just-in-time" appointment scheduler.

The present invention does not fully automate some administrator functions that provide information about the health plan (e.g., customer service and response to provider inquiries).

Preferably, the database lists for each insured the following types of information supplied during enrollment and updated as necessary: personal information, emergency information, current health status, family medical history, personal medical history, prescription drug history and health-relevant diet and exercise information.

For each medical provider enrolled in the health plan, the database preferably contains: provider identification number, personal information, medical office information, credentials, current prices and quality indicators. The database also contains a list of the insureds who are presently eligible to receive covered health care benefits under the plan, and it contains a record of the financial variables associated with each insured. This record includes coverage parameters, such as benefit amounts, deductibles and co-pays, as well as any health savings account transactions, and any balances outstanding to any providers.

The database can track prices, utilization, health care quality data, and it can systematize and maintain electronic medical records. It can be organized to provide lists based on geographic area and medical procedure; for example, a list of providers available to perform a designated procedure and each provider's charge for performing the designated procedure can be provided. The database also contains a suite of medical codes customarily used for identification and billing purposes.

A first processor can perform the following functions. Time stamp and process patient sign-in; confirm that the patient is eligible for benefits; request from the third processing means the insured's electronic medical record (EMR); administer any patient surveys that are scheduled; process quality indicators derived from the surveys; update the insured's EMR as a result of the current visit; archive a prototype treatment plan based on the treatment plan issued to the patient; produce a treatment plan; and produce for and distribute to insureds price, quality and credentials information on those providers who can provide the treatments needed by the insured.

A second processor can perform the following functions. Time stamp and process patient sign-in; confirm that the patient is eligible for benefits; request from the third processing means the insured's electronic medical record (EMR); administer any patient surveys that are scheduled; update the insured's EMR as a result of the current visit; and produce a treatment record.

A third processor can perform the following functions. Establish health care benefits for insured patients; maintain the eligibility records of insureds; maintain a record of provider credentials; maintain EMRs; maintain a record of provider prices charged for diagnostic tests, medical procedures and other goods and services transacted; collect treatment plans; collect treatment records; process medical claims; conduct a search for fraudulent transactions; maintain patient outcomes measures and other measures of health care quality; reconcile accounts of insureds, physicians and other providers; disburse payments to insureds, physicians and other providers; bill insureds for balances outstanding; and respond to changes in provider schedules with "just-in-time" rescheduling.

A fourth processor can enroll members into the health plan, and a fifth processor can enroll diagnostic physicians and treatment providers into the health plan.

It is an object of the present invention to provide a health plan administrator that is fully automated.

It is a further object of the present invention to provide an automated method for quantitatively evaluating patient outcomes that will facilitate comparisons of providers with regard to risk-adjusted patient outcomes on a diagnostic-specific basis.

It is a further object of the present invention to provide an automated method for quantitatively evaluating the accuracy and timeliness of diagnoses established by physicians.

It is a further object of the present invention to provide an automated method for quantitatively evaluating the complication rate of providers, especially those administering surgical procedures.

It is a further object of the present invention to provide an automated method for maintaining an archive of editable prototype treatment plans.

It is a further object of the present invention to provide an automated method for notifying patients if and when a change in a provider's schedule affects the time at which they are required to appear for a scheduled appointment.

One aspect of the present invention provides an apparatus and method that combines data from patients and physicians and applies a method that quantifies how quickly and completely a provider's patients recover. The method provides for the comparison of patient outcomes of different providers treating the same illness or injury.

Methods are also disclosed for treating co-morbidities and mortalities, which allow comparisons of risk-adjusted outcomes of the providers in the database.

Other aspects of the present invention to improve health care quality can provide incentives for accurate and rapid diagnoses, and the minimization of complications in treating patients, particularly with respect to surgical procedures.

Another aspect of the present invention reduces the average time and effort—and therefore the cost—required by the diagnostic physician to prepare written treatment plans.

A final aspect of the invention is a method for reducing the amount of time that patients must spend in the waiting room prior to seeing the provider.

DESCRIPTION OF THE DRAWINGS

FIG. 16 is a comparative report in accordance with an aspect of the present invention.

FIG. 17 shows credentials as part of a comparative report in accordance with an aspect of the present invention.

DETAILED DESCRIPTION OF THE INVENTION

Figure 1:
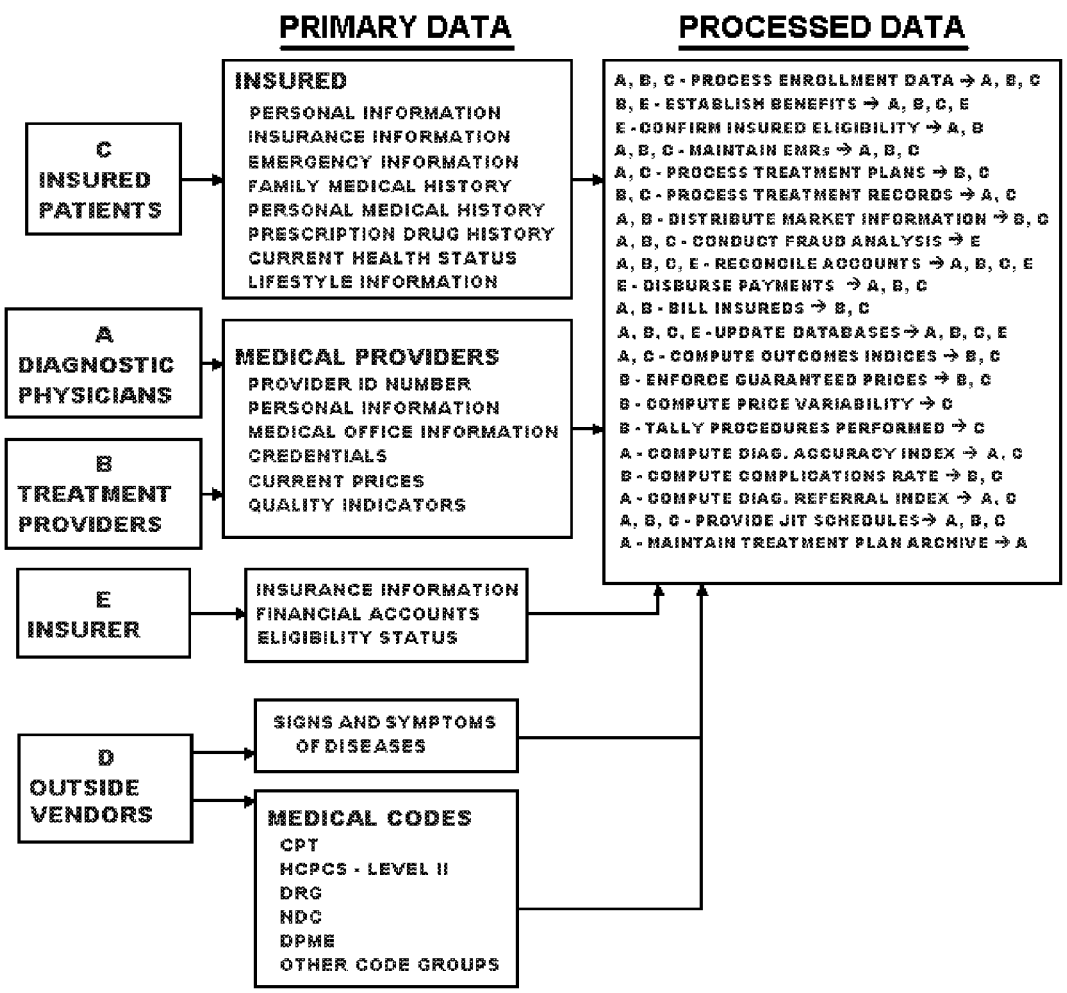
FIG. 1 illustrates a block diagram showing how the functions of a health plan administrator can be fully automated through an integrated database.

The following is a list of terms utilized throughout this specification:

Administrator: The entity that performs the tasks typically performed by the administrator of a health care plan, including but not limited to enrollment, eligibility confirmation, claims preparation, processing and adjudication, patient billing, account maintenance, database maintenance, and fraud detection.

Insurer: The entity that provides health insurance or a pre-paid health plan to a number of parties.

Insured: A party that is insured by the insurer, including the person and his or her dependents covered by a policy issued by the insurer. An insured who is not a dependent is the policyholder.

Patient: A person receiving health services.

Provider: Any person or entity providing medical or health-related services.

Physician: A doctor who conducts an initial or diagnostic examination of an insured to determine the patient's diagnosis and what medical services are needed.

PMN: Personal Medical Number, a unique number assigned to each insured for purposes of identification.

The following is a list of terms utilized in the part of this disclosure that describes the apparatus and methods that quantifies patient outcomes.

Survey: A set of statements or questions designed to quantify a patient's current health care status with respect to a specific illness or injury; or to establish a patient's satisfaction with one or more aspects of the health plan and its providers.

Survey Score: The numerical value of a completed survey.

Survey Score Set: One or more survey scores pertaining to a single illness or injury of a single patient.

Reference Recovery Functions: The statistically estimated curve that is fitted to a number of survey scores or survey score sets.

Prognosis Rating: A physician's predicted numerical value of a patient's recovery from a specific illness or injury.

Recovery Score: The numerical value of a patient's recovery, based on two or more survey scores.

Personal Recovery Function: A patient's interpolated recovery path that goes through each recovery score.

Outcomes Index: A numerical index derived from the recovery scores of a number of patients with the same diagnosis and with prognosis ratings within a given range.

U.S. Pat. No. 5,225,976 which is incorporated herein by reference in its entirety, made a fully automated health plan administrator possible by teaching how to produce an automated benefit payment process, which includes the processing of medical claims without incurring significant risk of failing to identify instances of overcharging, or unnecessary or inappropriate treatments. In one embodiment of the health plan described in that invention, the diagnosing physician would be either under contract to or an employee of the health plan. By separating the diagnostic function from the therapeutic function, and with the fealty of the former to the health plan, the therapeutic treatments in the treatment plan are, in effect, pre-authorized by the diagnostic physician. Therefore, while processing claims submitted by the treating provider, claims review need not be concerned with unnecessary or inappropriate treatments. Even if the health plan permits the medical treatment provider to pursue a different treatment protocol, as it would in one embodiment of that invention, as long as the total benefit amount remains fixed at the amount in the treatment plan issued by the diagnostic physician, no additional claims processing concerns arise.

Moreover, if benefit amounts are pre-established and fixed for each covered benefit, the claims review process need not be concerned with overcharging, as the insured is responsible for all charges in excess of the benefit amount. All of the remaining claims processing concerns can be fully automated.

The present invention extends the art by showing how to integrate with the automated benefit payment system all of the other tasks typically provided by the administrator of a health care plan that meet certain conditions, such as those described in the previous paragraph. These other tasks include but are not limited to: enrolling insureds into and removing them from the health plan; enrolling providers into and removing them from the health plan; establishing benefits; validating that patients are eligible to receive benefits under the health plan; and maintaining electronic medical records (EMRs). The customer service function of the plan administrator can also be automated, but in the preferred embodiment some manual intervention is desirable.

FIG. 1 illustrates how these functions are integrated through a database management system operated by the health plan administrator. As the figure shows, the automated administrator accepts data inputs from insured patients, diagnostic physicians, treatment providers, the insurer and outside vendors, which are labeled A through E. The middle column identifies the types of primary data and their source. For example, in the preferred embodiment, the insured patient (C) provides the types of information indicated through an on-line enrollment process. Alternatively, assisted enrollment can be offered at the offices of the diagnostic physicians and the treatment providers. Diagnostic physicians (A) and treatment providers (B) provide the types of information indicated also through an on-line enrollment process. The insurer of the health plan (E) provides a current list of eligible members, initial account/coverage information and the amount of funding added to various monetary accounts. Outside vendors (D) supply the medical code data sets that are used in the preparation of treatment plans and treatment records.

The enrollment information for insureds may include personal information, insurance information, emergency information (including blood type and person to notify), family medical history, personal medical history, medications, current health status, and relevant diet and exercise information. This information can also be organized and written to a magnetic medium, such as a floppy disk or flash drive, which preferably can be kept in the physical possession of the insured. In the preferred embodiment, the information is recorded at the time of enrollment on the fourth processing means 6, as shown in FIG. 2.

The box in the third column of FIG. 1 shows the various tasks performed by the automated administrator. The letter(s) at the beginning of each item refer to the boxes in the first column and identify the source of primary data used to produce the information, and the letter(s) at the end of each item identify the users of the produced information. Some of the listed tasks (e.g., compute price variability, compute diagnostic referral index) pertain to performance measures in an existing embodiment of the present invention that are optional and are not further explained in this application. These tasks have all been coordinated, such that none requires manual intervention by the health plan administrator.

Figure 2:
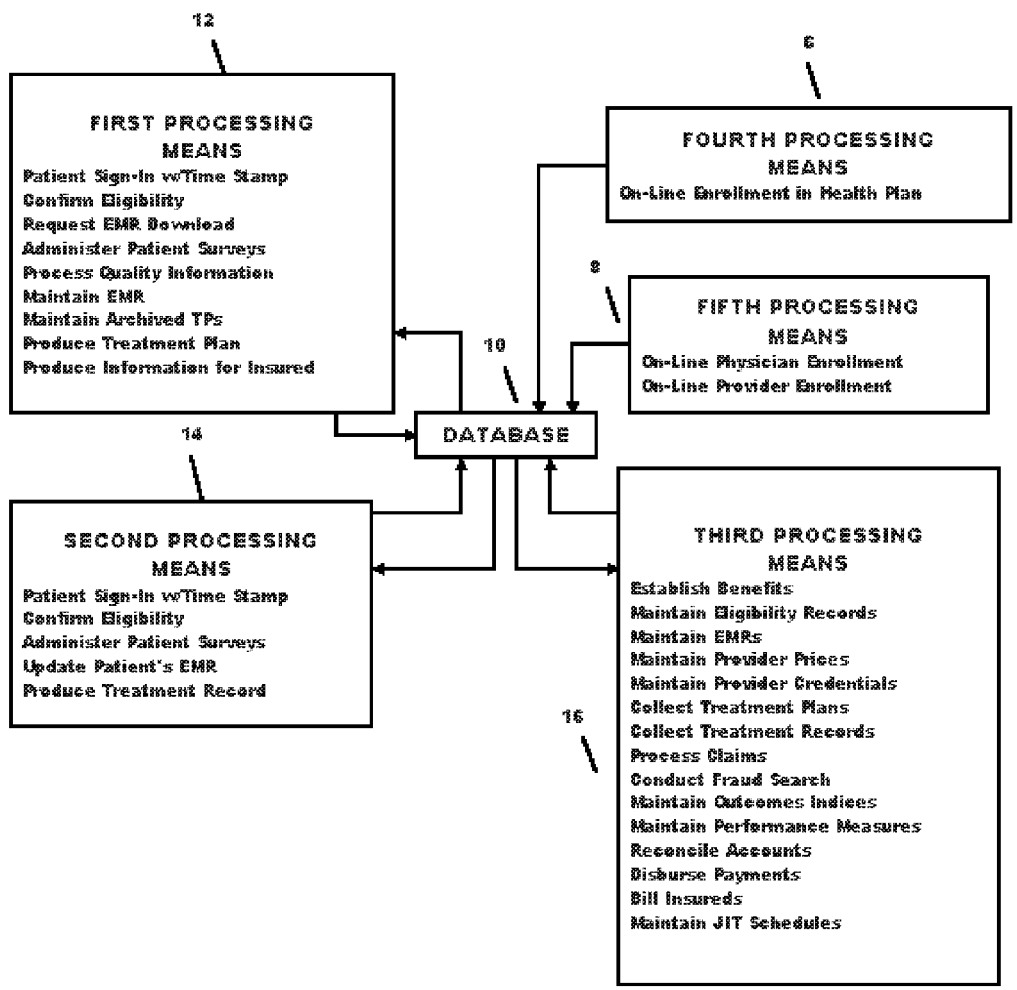
FIG. 2 illustrates a block diagram showing an overview of a fully automated health plan administrator.

FIG. 2 is a block diagram showing the distribution of tasks by processing means, and the relationship between the processing means and the central database. In accordance with the preferred embodiment of the present invention, a fourth processing means 6 is accessed for enrolling insureds into the plan on-line, and a fifth processing means 8 is accessed by physicians and providers to enroll in the plan on-line. The enrollment information is processed and stored in the database 10. The fourth and fifth processing means may be any electronic input device with access to the third processing means 16. Possible input devices include the first processing means 12 and the second processing means 14, as well as a home computer.

The tasks of the third processing means 16 are numerous. First, it must establish a benefit amount for every covered procedure and other covered benefits. In the preferred embodiment, the level of benefits is expressed as a percentage and refers to the percentage of providers of a particular benefit whose prices are less than or equal to the benefit amount. For example, a benefit level of 65 percent means that 65 percent of the providers within the local health care market charge no more than the benefit amount for covered procedures. This method for establishing benefits retains flexibility and readily lends itself to an automated process. To establish the benefit amount for a procedure, the third processing means 16 ranks providers of that procedure according to price, with the most expensive provider at the top of the list. The most expensive provider among the bottom 65 percent of providers is identified. The price of that provider becomes the benefit amount for that procedure. The same method is then applied to all of the other procedures and covered benefits.

A second task is to maintain a list of insureds who are presently eligible to receive benefits under the health plan. In the preferred embodiment, the third processing means receives a data file or other electronic record at least daily from the insurer, showing additions and removals from the eligibility list and revisions in insureds' benefits and coverage. A condition of eligibility is that the insured's health insurance premiums are current.

Another task for the third processing means 16 is to maintain the electronic medical records of the insureds. These records are maintained in the database 10 and are created during enrollment. EMRs preferably include: information obtained during enrollment, as well as updates and other revisions; treatment plans and treatment records; prescription drug records; medical images (e.g., x-rays, CT scans, MRIs); laboratory records; medical providers' notes; communications; consultation reports, and referral records. The EMR is modified when a diagnostic test or procedure is performed, when prescriptions are filled, and when medical claims based on these plans and records are processed. This task demonstrates the high degree of task integration required to achieve full automation of the health plan administrator.

The next eleven tasks shown for the third processing means 16 in FIG. 2 are taught by U.S. Pat. Nos. 5,225,976 and 5,519,607 which are both incorporated herein by reference in their entirety. These tasks are described in the following.

Figure 3:
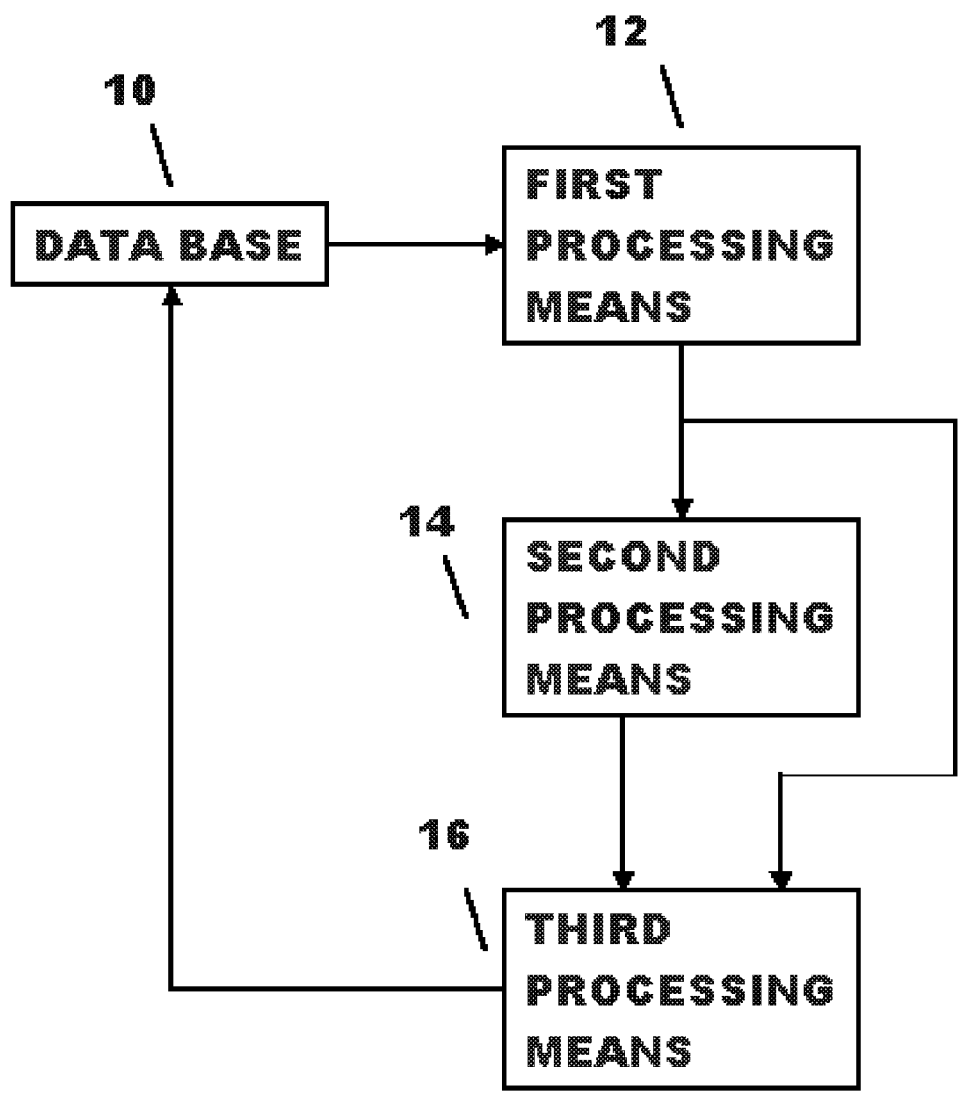
FIG. 3 illustrates a block diagram of an automated health benefit processing system in accordance with U.S. Pat. No. 5,225,976.

The claims result when an insured—including the insured person and any dependents covered by the policy—seeks medical services. The system, as illustrated in FIG. 3, includes the database 10, a first processing means 12, a second processing means 14 and the third processing means 16.

The database 10 preferably specifies information for each relevant geographic area and for each medical procedure. This information includes a fixed benefit or payment payable to an insured if the procedure is prescribed and performed, a list of medical service providers able to perform the procedure and the price charged by each provider for that medical procedure.

The listed price in the database 10 can be a price recently charged by the provider. For example, the listed price can be the price charged by a provider on the most recent insurance claim. In this example, the listed price in the database 10 is updated each time a claim is processed by the system of FIG. 3. If such frequent updating creates system difficulties, the database 10 can be alternatively be updated at a regular interval. In a preferred embodiment, however, the listed price in the database 10 is a guaranteed price that is agreed to by the provider.

The applicable geographic area is the area wherein a patient can conveniently travel to obtain the service. The providers listed in the database 10 include physicians, dentists, hospitals, optometrists, pharmacies, testing laboratories and any other entity at which a patient can incur expenses that are covered under the insured's policy.

It is further preferred to include credentials and other background information concerning each provider in the database 10, much of which is recorded during initial enrollment. For example, for each provider, it is preferred to include medical specialties and board certification, number of years in practice, medical degrees with class rank, residency location, the number of malpractice suits lost and settled, any hospital affiliations, any university affiliations as well as any credit cards by which payment can be made. Also, the number of times the provider has performed the procedure within a given amount of time, for example, one year, can be provided. Since this last information is analyzed by the third processing means 16 when claims are processed, the number of times the procedure has been performed can be updated every time a claim is processed or periodically on a less frequent basis. The third processing means updates this information as needed with input from the fifth processing means 8.

The database 10 can be sorted by type of medical procedure, in which case, every provider of each medical procedure and related information is listed. In this case, it is preferred to refer to each medical procedure by a coded number, which is generally referred to by the medical industry as a Current Procedural Terminology (CPT) code or a Healthcare Common Procedure Coding System (HCPCS) code.

The database 10 can also specify medical diagnostic codes and descriptions associated with a particular episode of illness or injury. In this case, it is preferred to refer to each medical diagnosis by means of a coded number. Two sets of codes are in common use: International Classification of Diseases (ICD) codes and Diagnostic-Related Group (DRG) codes. ICD codes are diagnostic codes, while DRG codes are associated primarily with Medicare. When information is classified under DRG codes in the database 10, it is preferred to indicate providers capable of performing, or assuming responsibility for, the full range of procedures for treating the indicated episode of illness or injury, to the extent possible. Preferably, the database 10 includes the information stored under CPT, HCPCS and DRG codes so that claims can be processed when any or all codes are specified. The database 10 also preferably includes, for each code, a description thereof.

Figure 11:
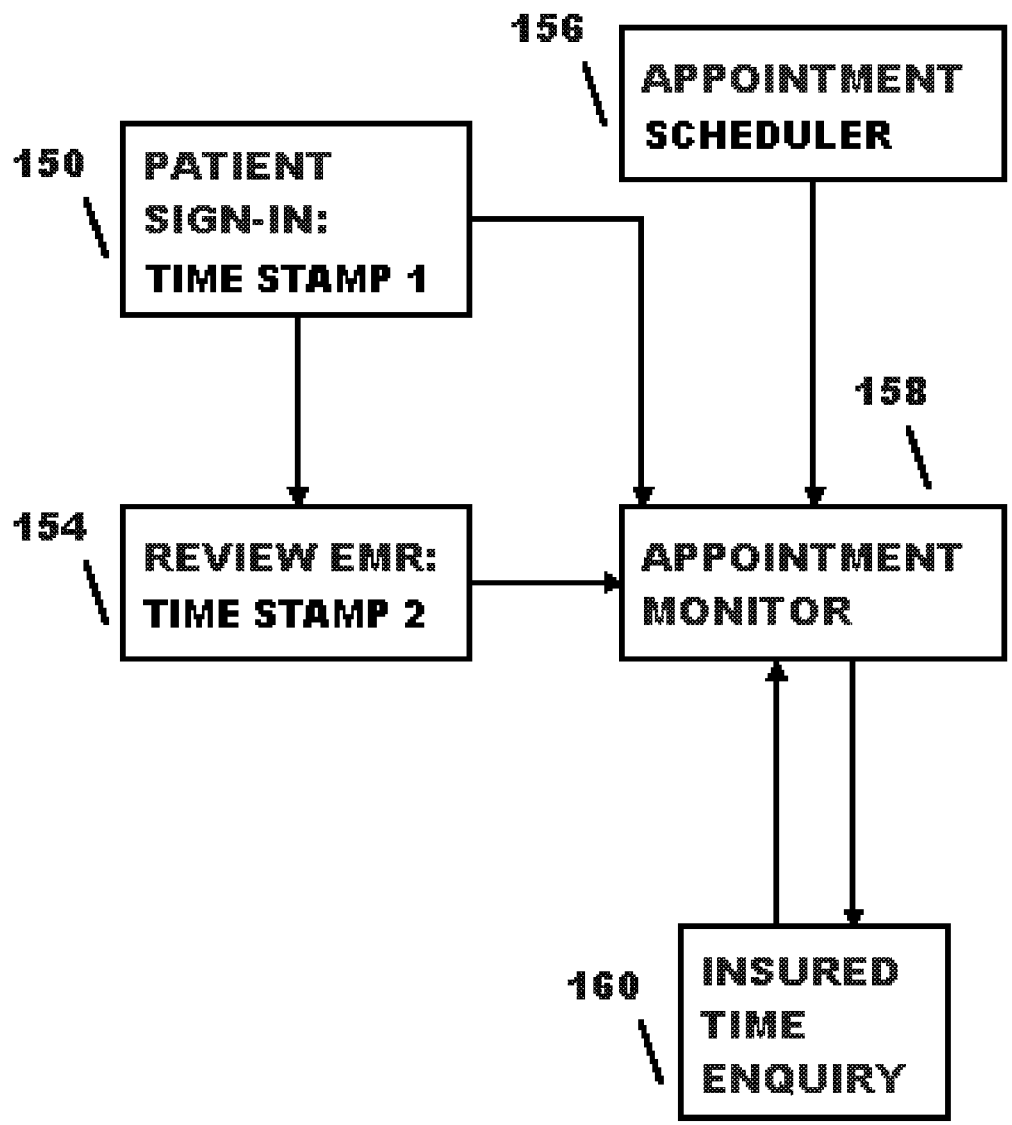
FIG. 11 illustrates a diagram of a just-in-time appointment scheduler in accordance with another element of the present invention.

In the preferred embodiment of the present invention shown in FIG. 11, a method is described for automatically reducing wait times at the offices of medical providers. An appointment monitor 158 obtains the current day's appointments from the provider's electronic appointment scheduler 156. When a patient signs in 150 at a provider's office, the appointment monitor 158 records the time, and it also records that the patient's appointment has been kept.

Shortly prior to examining the patient, the provider will review the patient's electronic medical record (EMR) 154. In the preferred embodiment, the time at which the provider begins his review of the EMR will be recorded by the appointment monitor 158. The monitor now has sufficient information to assess and revise the appointment schedule. A patient's revised appointment time will depend on: 1) the number and duration of appointments scheduled prior to that of the patient, and whom the provider has not yet seen, 2) the time necessary for the patient to complete any surveys, 3) the time necessary for the patient to be processed in by a nurse or other assistant, and 4) a buffer period. The buffer period is a time period that is added to the other times, 1-3. The buffer period is of sufficient length to ensure that the provider will likely not be delayed in administering health care. The purpose of the buffer period is to accommodate cancellations, examinations and procedures that take less time than scheduled, as well as patients that show up late for an appointment.

In the preferred embodiment, an insured patient 160 on the current day's schedule can contact the appointment monitor 158 by telephone or electronically (e.g., e-mail, cell phone, or internet) to receive a voice or text message informing the patient of his/her current appointment time, where "current" means as of the time of the inquiry.

In another embodiment, the appointment monitor 158 can contact by telephone or electronically some or all remaining appointments whenever the current day's schedule is revised. These appointments would be informed of revised appointment times without any initiating inquiry. If there is a cancellation, the monitor 158 could, in another embodiment, electronically contact later appointments, advising of the availability of an earlier appointment time, assuming that the scheduled appointment durations are compatible.

After recording the patient's sign-in time, the first processing means 12 sends a request to the third processing means 16 to send electronically the patient's medical records. After reviewing the patient's medical records, the physician conducts a diagnostic examination of the insured patient. Through the examination, the physician determines the medical services and pharmaceutical prescriptions that are needed to treat the insured.

Figure 4:
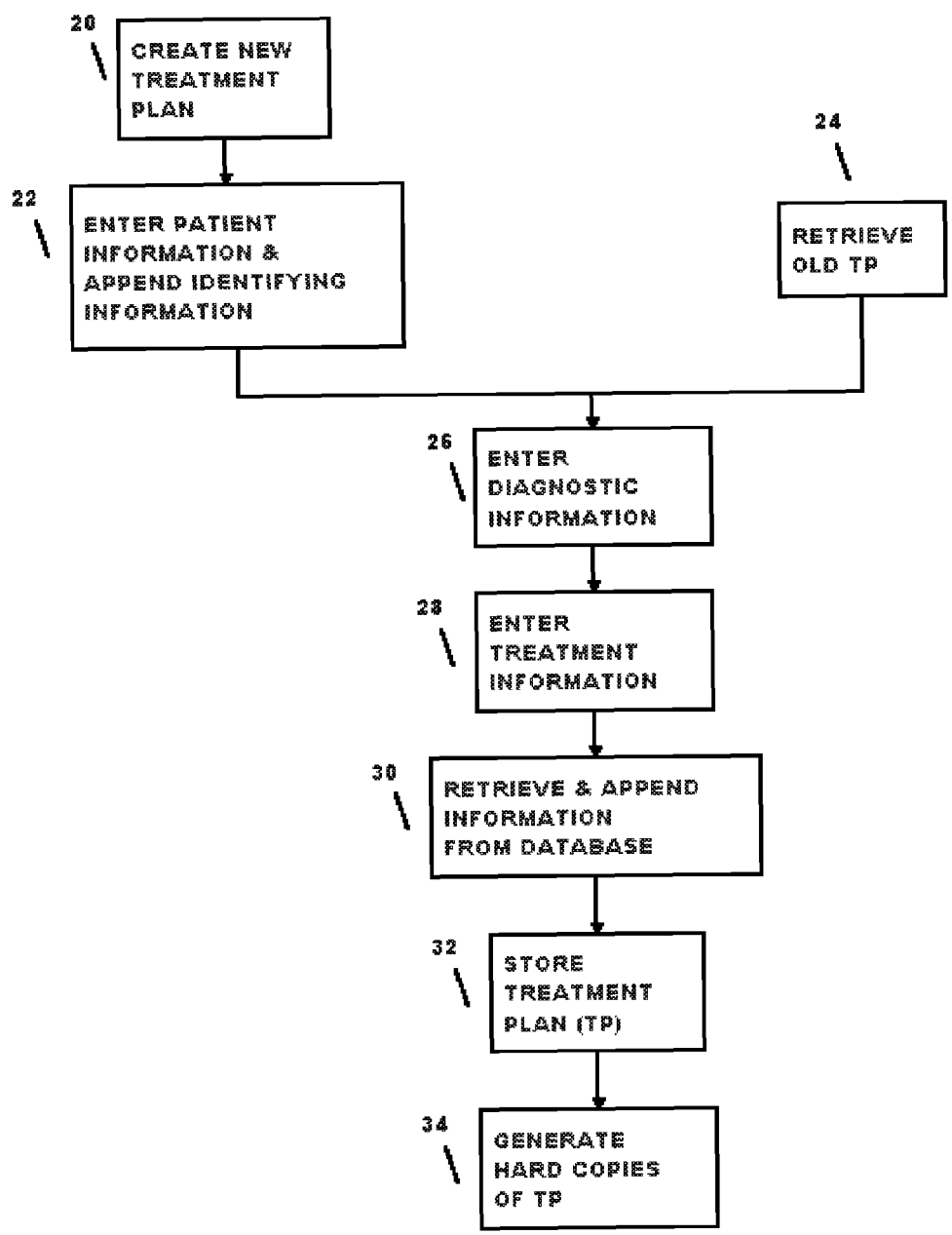
FIG. 4 illustrates a preferred procedure used by the fully automated health plan administrator of FIG. 1 to generate a treatment plan.

After the examination, if necessary, the physician generates a treatment plan for the insured patient on the first processing means 12 in accordance with a preferred procedure illustrated in FIG. 4. If this is the insured patient's first examination for a particular illness or injury, then a new treatment plan is created in step 20, and information concerning the patient is automatically entered into the treatment plan in step 22, based on the patient's personal medical number (PMN), which is recognized during patient sign-in. This information preferably includes, in addition to the PMN, the patient's and the insured's name, address and phone number. The first processing means 12, in step 22, also automatically appends additional identifying information to the treatment plan. Preferably, the physician's identification number and the examination date and time are added, and a unique number is assigned to the treatment plan. Also appended are the insurer's name and the status of the treatment plan (i.e., new or continuing).

If the patient is consulting the physician concerning an illness or injury for which a treatment plan has already been generated, however, that treatment plan is retrieved in step 24. Since the patient information and the identifying information have already been added to this treatment plan, step 22 need not be repeated.

Figure 12:
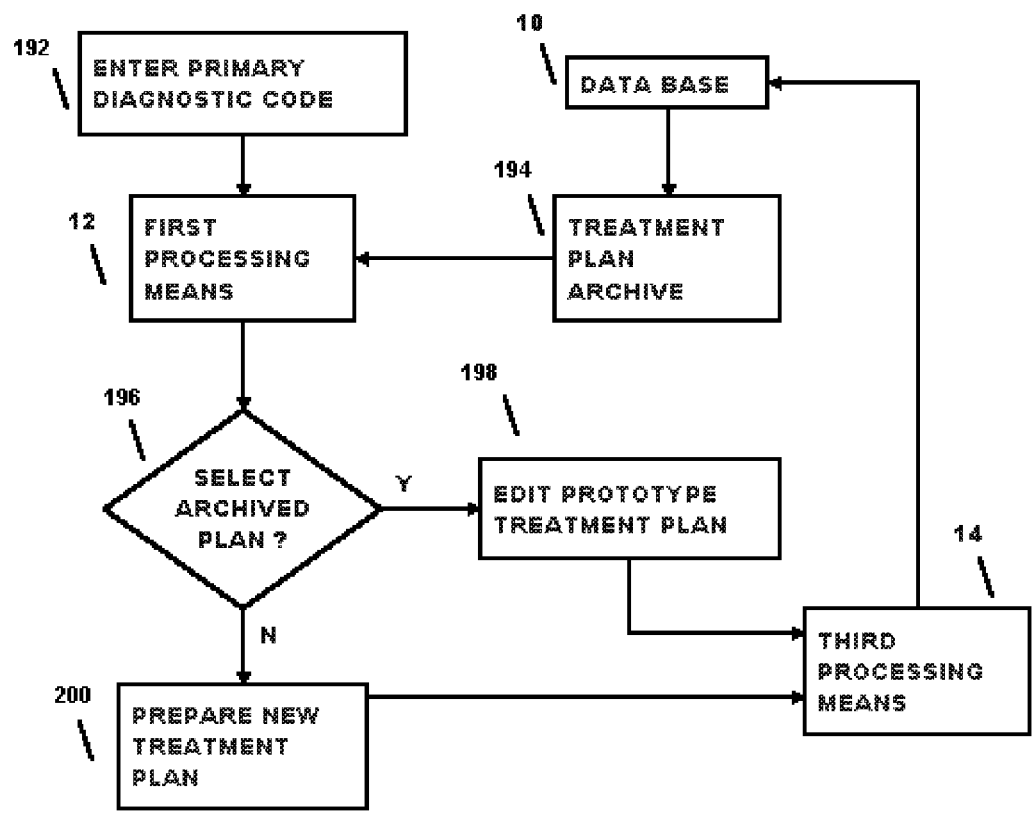
FIG. 12 illustrates a diagram of a method for creating and maintaining an archive of editable prototype treatment plans in accordance with another element of the present invention.

In step 26, one or more ICD codes or DRG codes designating the episode of the illness or injury requiring treatment (i.e., the diagnosis) is preferably entered, based on the examination of the patient, diagnostic test results and any other diagnostic information. Also, observed symptoms can be included in the treatment plan during this step. In step 28, the physician may access an archive (step 194, at FIG. 12) containing treatment plans that have been previously developed for the primary diagnostic code just entered 192. Upon selecting an archived treatment plan 196, the physician may modify it 198; alternatively, he may choose to prepare a new treatment plan 200 from scratch. In either case, he may choose to archive the modified/new treatment plan. An existing or new treatment plan can be archived by stripping a copy of the treatment plan of all information except the treatment codes, modifiers/qualifiers, descriptions and frequencies; and, optionally, except the drug codes, descriptions, specifications, quantities, refills and frequencies. This record is named and stored so that it can be readily retrieved whenever a similar case presents itself to the physician. Alternatively, in step 28 at FIG. 4, information concerning the treatment recommended as a result of the diagnostic examination is entered into the treatment plan. CPT code numbers designating the medical treatment procedures to be performed are also preferably entered into the first processing means 12. Also, any pharmaceutical prescriptions are entered. Finally, the recommended frequency of treatment (e.g., two times a week) and the recommended duration of each treatment (e.g., one month) are entered into the first processing means 12, as are drug codes, descriptions, specifications, quantities, dosages, frequencies and refills for pharmaceutical prescriptions.

In step 30, the first processing means 12 accesses the database 10 using the CPT codes and the DRG or ICD code previously entered in the treatment plan in step 26 to retrieve the information stored in the database 10. The retrieved information includes a list of providers able to perform the services specified by the CPT codes and their associated prices. Background information concerning each provider, if available, is also retrieved. It is further preferred that the information in the database 10 be accessed based on the geographic location convenient to the patient's residence. The information retrieved from the database 10 is appended to the treatment plan.

The first processing means 12, in step 32, stores the treatment plan as generated in steps 26, 28 and 30. It is preferred to store the generated treatment plan with all other treatment plans generated that day in a directory for later transfer to the third processing means 16. A copy of the treatment plan is also preferably stored on separate magnetic mediums, such as a hard disk for the physician and a floppy disk or flash drive for the patient.

Next, the first processing means 12 produces hard copies of the treatment plan in step 34. The hard copies are preferably distributed as follows: Two copies are distributed to the patient, a first to be given to a medical services provider to refer to and a second for the insured's records; a third copy is transmitted directly to the Administrator; and a fourth copy is retained by the physician for his records. These multiple copies are used for fraud detection and are not needed by the system to process claims, unless the provider lacks the capability to read electronically the patient's copy of the treatment plan, or to receive a copy of the treatment plan from the third processing means. In this case, a hard copy of the treatment plan can be provided by the patient.

The treatment plan and the appended provider information, therefore, are available for review by the patient to assist the patient's decision-making process. For example, the patient can determine the benefit payable for the medical procedures to be performed. The patient can also determine the price each provider will charge for performing the procedures, whether it is a guaranteed price or some current price, and make a selection accordingly. As taught in U.S. Pat. No. 5,519,607, the patient can also review the outcomes of each provider, if available. This assists the patient in assessing the value of the services being offered. Additionally, if background information is available concerning the providers, then the patient can make a more informed selection as to the likely quality of the services to be provided.

The first processing means 12 can also include a diagnostic software package as well as a diagnostic database to assist in the diagnostic examination. The software package can be any of the available artificial intelligence medical diagnoses systems. The diagnostic database would preferably associate sets of symptoms to specific diagnoses. These associations would be a statistically based system that would be updated by the third processing means 16 as claims are processed. For example, the set of symptoms and the associated diagnosis can be determined from previously completed treatment plans. The appropriateness of the diagnosis can be determined from later treatment and can be included in the diagnostic database. Such a database would be generated during claims processing by the third processing means 16 from information derived from the treatment plans and subsequent treatments.

When the patient seeks a provider to perform the medical procedures listed in the treatment plan, the patient can instruct the office of the physician where the treatment plan was generated to have the first processing means 12 electronically send the treatment plan to the second processing means 14 which will be used by the selected provider to further process the patient's claim. Alternatively, a magnetic medium or hard copy of the treatment plan can be given to the provider by the patient, or the treatment plan can be obtained from processing means 16.

The second processing means 14 can either be in the provider's office or can be a centrally located processor to which all providers have access through data entry means in the providers' office. In the case of a centrally located second processing means 14, the first processing means 12 can automatically transmit the treatment plan to the second processing means 14 once the plan is complete. Then, regardless of which provider is sought, the information will be accessible. Further in the case of centrally provided second processing means 14, to reduce the potential for fraud, it is preferred that the provider's access to treatment plans be limited to the treatment plan for the patient being treated. This can be accomplished by providing access codes for each treatment plan which the provider learns from the patient or from the third processing means.

Figure 5:
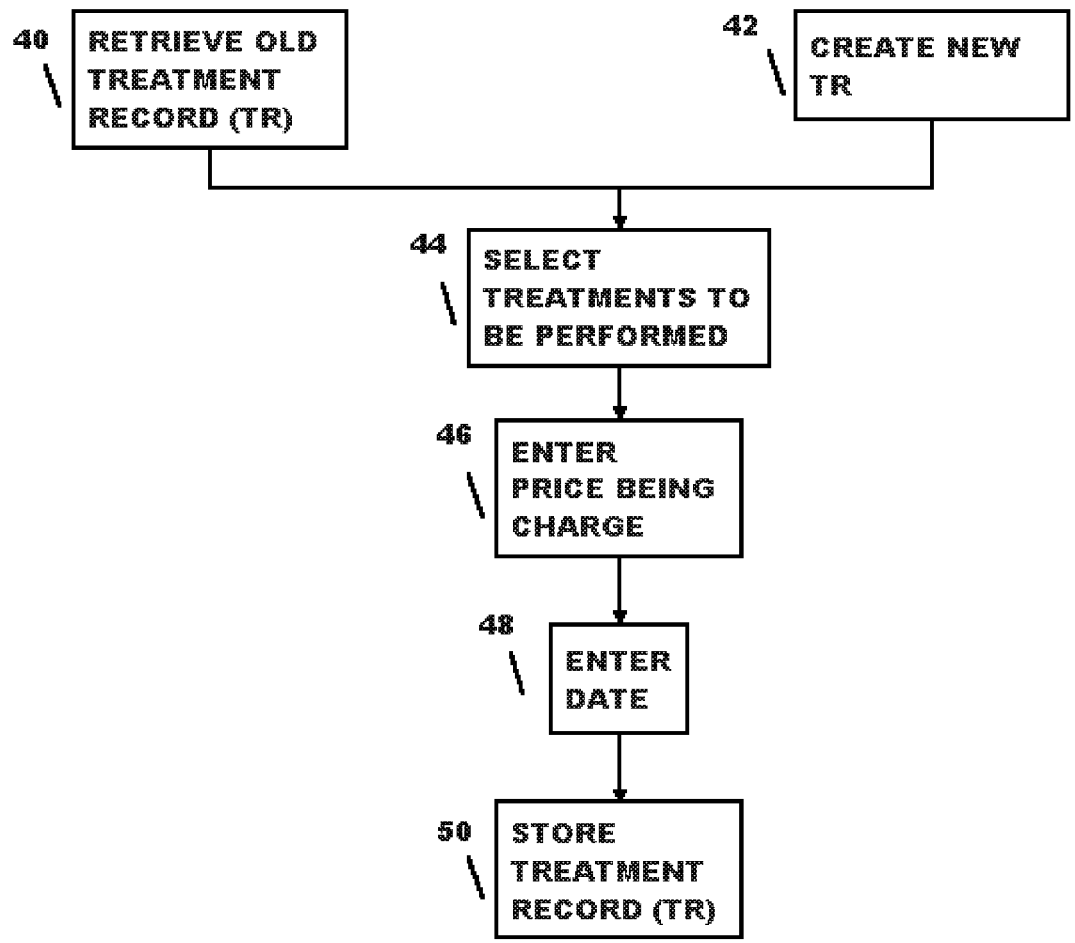
FIG. 5 illustrates a preferred procedure used by the fully automated health plan administrator of FIG. 1 to generate a treatment record.
Figure 6:
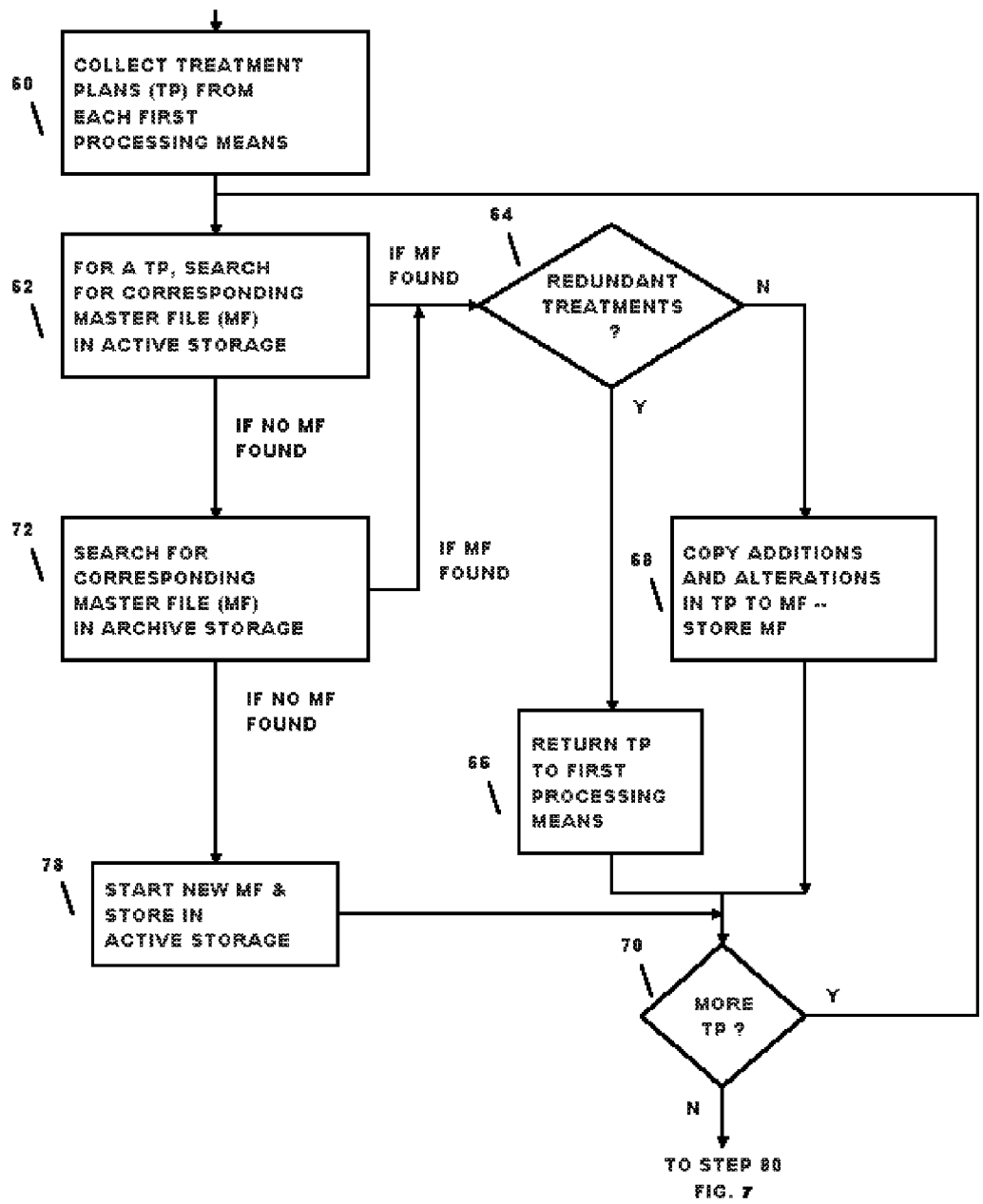
FIGS. 6 through 9 illustrate the processing of treatment plans and treatment records in accordance with a preferred embodiment of U.S. Pat. No. 5,225,976.

Once the treatment plan is received, the provider reviews the plan and determines if prior treatment has been performed by him. Referring to FIG. 5, if there has been prior treatment, then the second processing means 14, in step 40, searches for and retrieves a treatment record for reference. If this is the first treatment for an illness or injury, then a new treatment record is generated in step 42 on the second processing means 14. In step 42, the second processing means 14 also preferably automatically includes as part of the treatment record identifying information such as the name of the provider and/or his firm's name, the provider's identification number and address. Also included is a treatment record identification number associated with the treatment plan identification number, the patient's and the insured's name, address, phone number, e-mail address and personal medical number.

The provider then reviews the treatment plan, any available treatment record previously generated by the provider and any available test results (e.g., x-rays, lab tests) to determine if the diagnosis in the treatment plan is acceptable. The second processing means 14 can also include the diagnostic database previously described as well as any other diagnostic software package which can analyze the information in the treatment record and the treatment plan to assist the provider in this determination. If the provider disagrees with the diagnosis and the recommended treatment plan, the provider and the physician that generated the treatment plan confer. Any resulting changes are indicated in the treatment plan.

The provider, in step 44, selects the treatments to be performed on the current date by selecting associated CPT or DRG codes from the treatment plan. Also, if any pharmaceutical prescriptions are necessary, they are entered and the prescription given to the patient and processed in the same fashion as previously described in relation to the first processing means 12. In step 46, the provider's charge for performing the medical procedure or procedures is entered into the second processing means 14. If this price is guaranteed, then it should match the price listed in the database 10. If the price is not guaranteed, then it may or may not match the listed price. In step 48, the date on which the procedures were completed is entered. Once any procedures are completed, the treatment record may be stored in step 50 into a directory in the second processing means 14 along with all other unprocessed treatment records for eventual transfer to the third processing means 16.

Referring to FIGS. 6 to 9, the processing by the third processing means 16, of the treatment plans generated on the first processing means 12 and of the treatment records generated on the second processing means 14, is described. This processing includes several checks for consistency (e.g., that dates of previously processed treatments have not been altered 94); data entry errors (e.g., that the price charged does not exceed the guaranteed price 98); stale information (e.g., that the patient's address or phone number has not changed 95); and fraudulent entries (e.g., that every treatment specified in the treatment record also appears in the master file 93). The third processing means 16, in step 60, periodically contacts each first processing means 12 via some communications network to collect each treatment plan that has been generated. As the treatment plans are collected, each treatment plan is processed as follows. In step 62, the active storage area in the third processing means 16 is examined to see if there is a master file with the same identification number as the treatment plan. The master files are files containing records of previous treatments related to this treatment plan. This search is performed to determine if related treatment plans or records have been previously produced. The active storage area in the third processing means 16 stores master files that are active or are transitional. An active master file has at least one treatment with a specified duration that extends beyond the current date. In a transitional master file, all treatments should have been performed within a predetermined amount of time before the current date, for example, two months before the current date.

If a corresponding master file is located in the active storage area, then in step 64, the collected treatment plan and the corresponding master file are evaluated to determine if the new treatment specified in the treatment plan is redundant, thereby reducing the potential for fraudulent claims. If the treatment is redundant, in step 66, the treatment plan is returned to the first processing means 12 with a notice of rejection indicating the redundancy. The patient is also notified. If the treatments are not redundant, in step 68, the additions and the alterations in the collected treatment plan are copied into the corresponding master file and the master file is stored. The next treatment plan is then retrieved in step 70.

If a master file is not found in the active storage area in step 62, then in step 72, the archive storage area is searched for a corresponding master file. The archive storage area contains archived master files that have been completed or which have treatments that should have been performed before the above mentioned predetermined amount of time before the current date. If a corresponding master file is found in the archive storage area, then steps 64, 66 and 68 are performed as needed.

If a corresponding master file is not found in archive storage area in step 72, then a new master file is generated by the third processing means 16 in step 78. It is generated by copying the relevant information from the treatment plan into the master file. Additionally, the master file is stored in the active storage area and the collected treatment plan is discarded.

Figure 7:
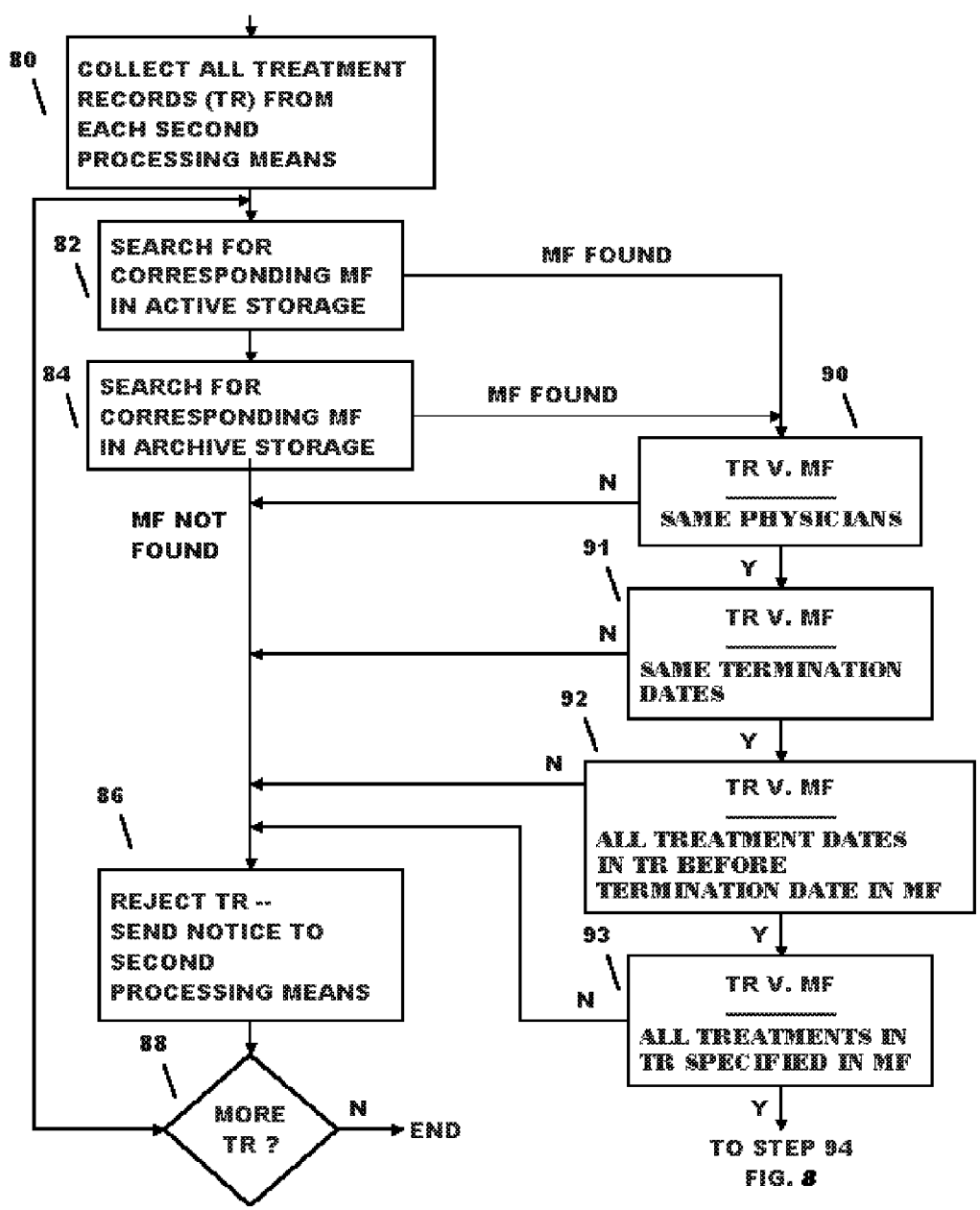

The above analysis continues until all collected treatment plans have been analyzed. Referring to FIG. 7, once all treatment plans have been analyzed, the third processing means 16 collects all of the generated treatment records from each second processing means 14, preferably via some communications network. Then, in step 82, the third processing means 16 examines the active storage area to determine if there is a corresponding master file. This is accomplished by examining the master file's identification number which is the same as the identification number in the related treatment plan and comparing it to the treatment record identification number.

If a corresponding master file is not found in the active storage area, then in step 84, the archived storage area is searched for a corresponding master file. If none is found, then in step 86, the treatment record is rejected and a notice of rejection is sent to the second processing means 14 indicating the reason for rejection. Then, in step 88, the next treatment record, if any, is sought for processing.

If a master file that corresponds to a collected treatment record is found in either the active or the archive storage areas, a series of security checks in steps 90 to 93 are performed by comparing the treatment record to the corresponding master file. In step 90, the comparison is made to determine if the same diagnostic physician is specified in the treatment record and in the master file. In step 91, the comparison is made to determine if the expiration dates in the treatment record and in the master file agree. In step 92, the comparison is made to determine whether the treatment date of the procedures in the treatment record are on or before the corresponding expiration date in the master file. In step 93, the treatment record is examined to verify that the treatments performed were specified by the master file. If the comparison in steps 90 or 91 do not match or if step 92 finds a treatment date after the termination date or if step 93 finds an unspecified procedure, all or part of the treatment record is rejected by the third processing means 16 in step 86 and a notice of rejection is sent to the second processing means indicating the reason(s) for the rejection.

Figure 8:
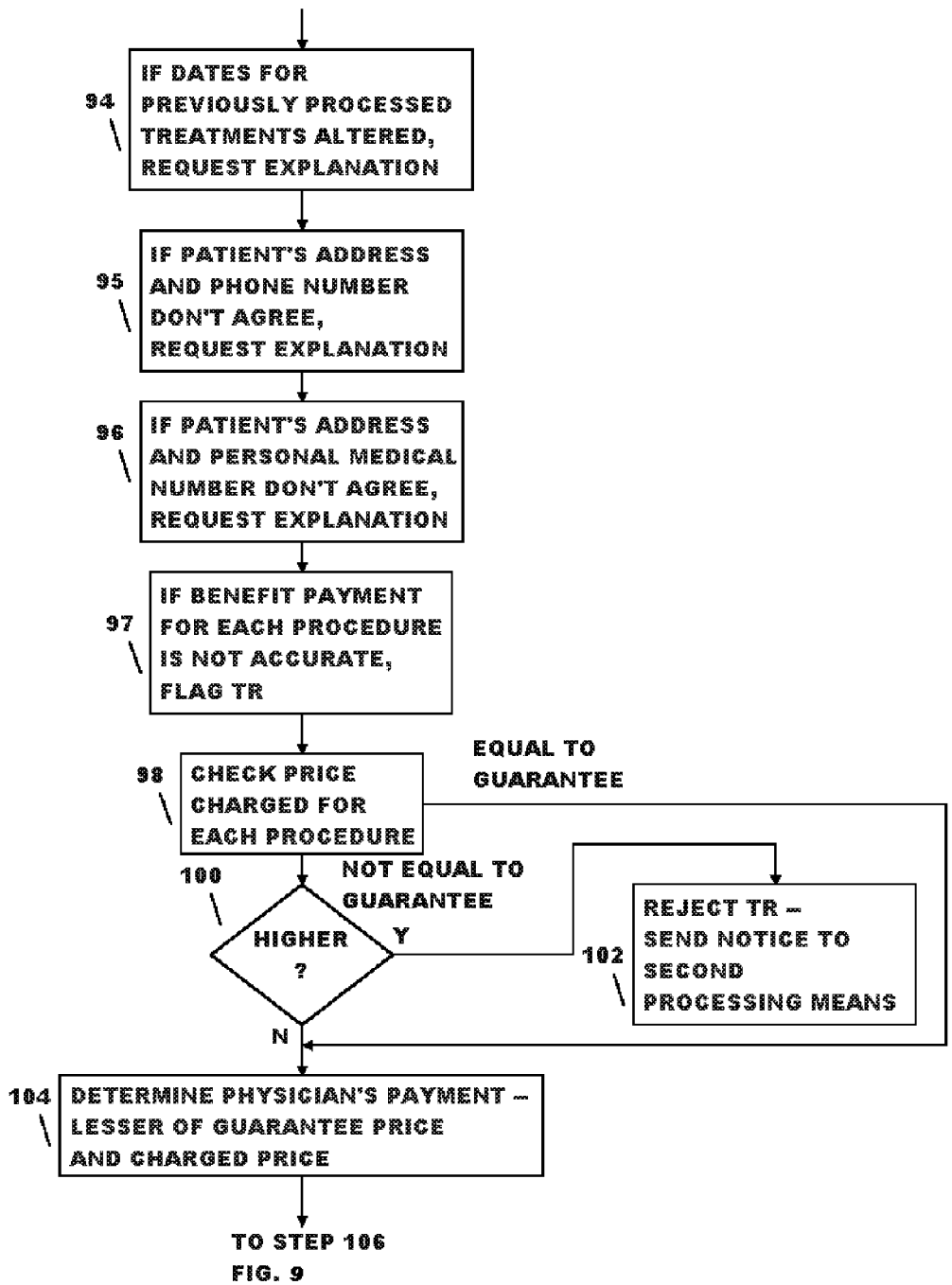

Referring to FIG. 8 if the security checks performed in the processing steps 90 to 93 are passed, then in step 94, the treatment dates in the master file associated with previously processed treatments are examined to see if alterations have been made. If they have, a request for explanation is sent to the second processing means 14. Next, in step 95, the master file and the treatment record are compared to see if the patient's address and phone number information therein agree. In step 96, the master file and the treatment record are compared to see if the patient name and personal medical numbers therein agree. If, in steps 95 and 96, there is a disagreement, then a request for verification is sent to the second processing means 14.

The third processing means 16, in step 97, checks the database 10 to determine if the benefit payment for each procedure, as specified in the master file, is accurate. If a discrepancy is found, the treatment record is flagged so that an investigation into the reasons for the discrepancy can be started. Processing, however, continues regardless of whether a discrepancy is found.

In step 98, the third processing means 16 checks the amounts charged for each procedure to determine if they are in agreement with any guaranteed prices in the database 10. If they are not, in step 100, the third processing means 16 determines whether the amount charged is higher than the guaranteed price. If the amount charged is higher, then in step 102, all or part of the treatment record is rejected and a notice of rejection is sent to the second processing means 14. If the amount charged is lower than the guaranteed price, however, in step 104, the amount actually charged is utilized to determine the amount due to the second processing means. In this case, the physician will receive the lesser of the amount charged and the benefit payable.

If, in step 98 the amount charged is in agreement with the guaranteed price, that amount is utilized in step 104 to determine the amount due to the provider. In this case, therefore, the provider will receive the lesser of the guaranteed price in the database 10 and the benefit payable.

Figure 9:
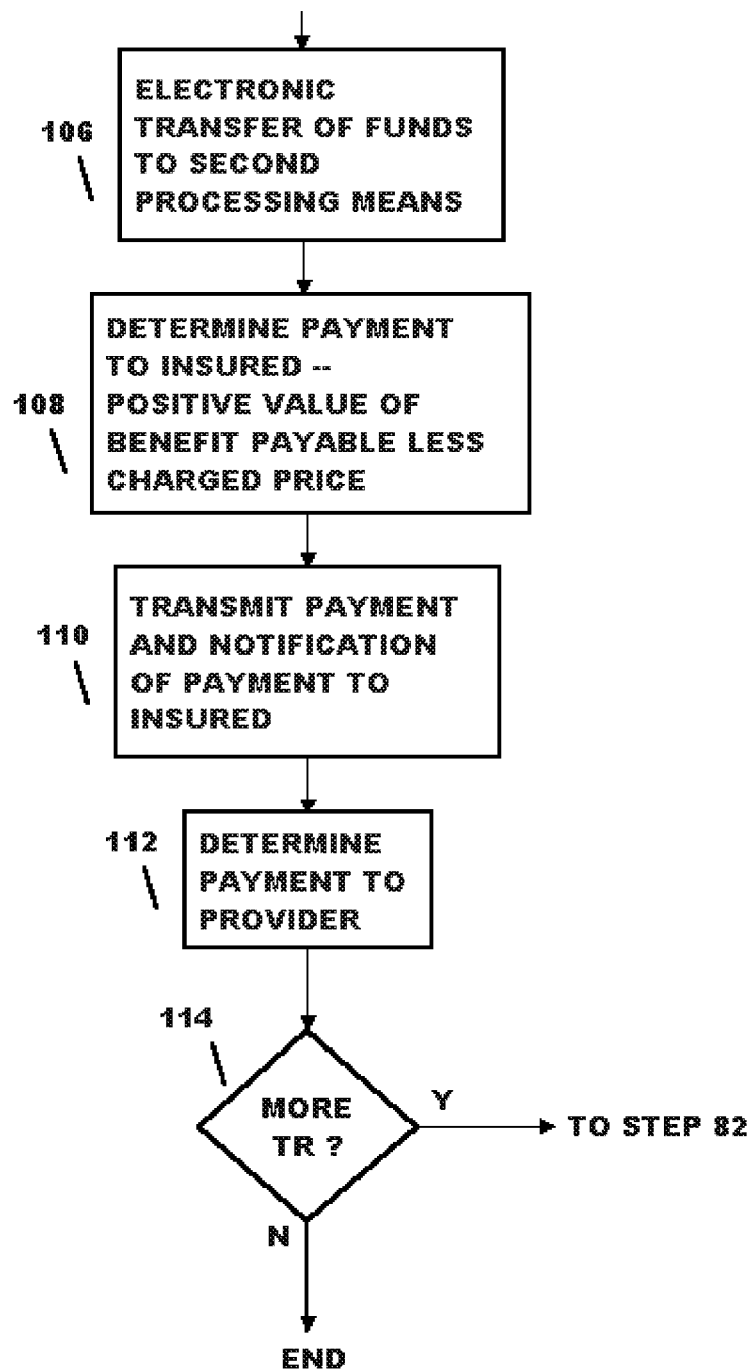

Referring to FIG. 9, in step 106, the amount due to the provider is preferably electronically transferred to the second processing means 14. The third processing means 16, in step 108, determines the amount due to the insured. This amount is the positive difference between the benefits payable for the procedures and the amounts charged. In step 110, a notification of payment to providers is issued to the insured along with a check for the amount due. If the amounts charged exceed the benefits payable, then the insured will be liable to the provider for this difference. In step 112, the master file is processed to determine the amount due the examining physician for procedures performed. Alternately, if the insured possesses a Health Savings Account, amounts due the insured can be credited to this account, and amounts owed by the insured can be debited to this account, given a sufficient balance. In step 114, the next treatment record, if any, is retrieved and is processed starting at step 82.

The third processing means 16, in addition to the processing illustrated in FIGS. 6 to 9, also performs background processing. For example, the diagnostic database previously mentioned can also be generated by extracting relevant information from treatment plans and treatment records. As another example, the termination dates associated with treatment plans can be modified by the examining physician when it is necessary to extend treatments. Such modifications are performed on a background basis. In addition, statistical evaluations could be performed on the diagnoses of the examining physicians to determine the reliability and completeness of the diagnoses. Similar analysis can be performed on all information received by the third processing means 16.

The steps illustrated in FIGS. 8 and 9 are based on the preferred embodiment wherein the price listed in the database 10 is a guaranteed price. If the listed price is merely a current price, the procedure can be modified so that the physician would receive the lesser of the benefit payable and the charge price. In this case, the insured would receive the positive value of the benefit payable less the charged price.

The system of the present invention also has special advantages for pharmaceutical prescriptions. As previously noted, prescriptions preferably become part of the treatment plan generated by the examining physician. In accordance with the preferred embodiment, the first processing means 12 would also generate a separate file containing the prescription information.

Additionally, hard copies of the prescription can be produced automatically and signed by the examining physician, if so desired. In the preferred embodiment, the database 10 would include price and source information on pharmaceutical prescriptions. This information would be appended to the treatment plan to assist the patient in selecting the pharmacy at which the prescription will be purchased. If the size of the database 10 is limited, then a limited number of drugs, preferably those most frequently prescribed, as well as a limited number of suppliers, preferably those most conveniently located or exceptionally low priced, are included in the database 10. If information on a prescribed drug is not in the database 10, then the patient can obtain such information from a hard copy listing of sources and prices, which can, for example, be maintained at the examining physician's office. The information can also be obtained directly from the first processing means 12.

The prescription information can be transmitted by the first processing means 12 directly to the second processing means 14 at the pharmacy. Alternatively, the patient can provide the selected pharmacist with the prescription on magnetic medium or on the hard copy. It is preferred that the second processing means 14 in the pharmacy contain a database that has background information concerning each prescription, such as warnings. When the prescription is filled and a label is printed out for the prescription, the database is accessed so that the warning information can be printed out on the label or on a separate listing. The information can also be provided in a database in the first processing means 12 and can be appended to the treatment plan. The processing by the second processing means 14 at a pharmacy is similar to that previously described. The processing by the third processing means 16 of the claims by the pharmacy is accomplished in the same way as described in relation to FIGS. 6 to 9.

Referring back to FIG. 3, such a system can be implemented in a variety of ways. In a preferred embodiment, a distributed processing system is used to prevent fraud. The first processing means 12 is provided in the offices of each physician performing diagnostic examinations, and the second processing means 14 is provided in the offices of each provider performing medical treatment procedures. The interconnections between the database 10 and each processing means in each office are provided as illustrated in FIG. 3 via some communications network. The database 10 is preferably provided in each first processing means 12, but can also be provided in the third processing means 16 for access by each first processing means 12. In an alternative embodiment the database 10, the first processing means 12, the second processing means 14 and the third processing means 16 can be part of a central processor. In this case, data entry means are provided in the office of each physician who performs diagnostic examinations to provide access to the first processing means 12 in the central processor. Also, data entry means are provided in the office of each provider who performs medical procedures to permit access to the second processing means 14.

Another benefit of this processing system is that an electronic medical record can be generated for each insured patient. This medical record will include the patient's medical history and can be used by the patient, the examining physician and the medical treatment provider alike. For example, when a patient visits an examining physician, that physician may review the patient's medical history to assist in the examination and diagnosis of any problem.

The formation of the patient's electronic medical record will now be discussed with reference to FIG. 3 which illustrates first 12, second 14 and third 16 processing means, and a database 10. The database 10 contains each patient's medical history record. This record typically includes medical information that is not found in previous treatment plans or records. For example, it may include an emergency record that typically consists of the name of the family doctor, whom to notify in case of an emergency, drug allergies, serious illnesses, device or organ implants (e.g. a pacemaker), other medical information and religious preference.

The personal medical history typically includes other medical information that is not found in previous treatment plans or records. For example, childhood diseases and inoculations are typically included, as well as prior operations and major diseases. The patient's record also includes a clinical record that is generally derived from the information contained in prior treatment plans and treatment records. Therefore, the database 10 will typically include a complete medical history including, among other things, the patient's prescription drug history, laboratory test results, medical notes, and medical graphics such as X-rays, ECGs, and sonograms.

When an insured visits an examining physician, the examining physician can access the database 10 via the first processing means 12 to view the insured's prior medical history to assist in the examination. The patient's records can also be accessed and downloaded from the storage medium that the patient presents at sign-in. As previously discussed, once the examination is completed, a treatment plan may be generated on the first processing means 12. The first processing means 12 then accesses the database 10 to update the insured patient's record by adding the information from the new treatment plan to the database 10. Alternatively or in addition, this information can be transmitted to the third processing means 16 so that the third processing means 16 can in turn update the database 10. Also, the third processing means 16 can access the database 10 to add any information that was not available to the first 12 and second 14 processing means.

When the insured visits a medical service provider, such as a physician, a pharmacist or a therapist, a new treatment record is generated by the second processing means 14, as previously discussed. The information in the new treatment is also preferably added to the patient's record in the database 10 by the second processing means 14. The information from the treatment record can also be transmitted to the third processing means 16 by the second processing means 14 so that the third processing means 16 can in turn update the database 10.

The information in the database 10 can be stored on any type of storage media, for example, on floppy disk, flash drive or any other type of magnetic media. Therefore, the insured may maintain a copy of the portion of the database 10 containing the personal medical history, including the emergency record and the clinical record. The information in the database 10 can also be stored on a central processor and it is preferred that the third processor 16 maintain a copy of this portion of the database 10.

U.S. Pat. No. 5,519,607 teaches how this system can also incorporate a rating system that measures the quality of care provided to the insured. When a diagnostic physician is preparing the treatment plan utilizing the first processing means 12, as in step 20 shown in FIG. 4, the insured is assigned a prognosis rating which indicates the expected recovery response of the insured following a treatment program by a medical treatment provider of average ability. The prognosis rating is preferably a number on an arbitrary scale, say from zero to ten. A prognosis rating of ten would indicate the most optimistic prognosis, while progressively lower numbers would indicate that a less optimistic recovery is expected. The prognosis rating depends on the severity of the patient's illness, as well as other relevant risk factors, such as age, heavy smoking and co-morbidities. The prognosis rating can then be reported from the diagnostic physician to the patient in a separate document during step 28. Additionally, the prognosis rating is transmitted by the first processing means 12 to the third processing means 16.

The third processing means 16 then adds this information to the database 10. For each medical treatment provider, the database 10 will include information, i.e., an outcomes score or index, indicating how well insured patients having a given illness or injury and a given prognosis rating responded to the treatment; then, the actual outcome is compared with the expected outcome via some scoring method, which is a subject of the current patent application. As described earlier, the resulting information is then available for each insured patient to decide which medical treatment provider to select. For example, this information can then be presented to the insured in a graphical format showing, for each medical treatment provider, the prognosis rating on the vertical axis and the outcomes score on the horizontal axis.

Figure 10:
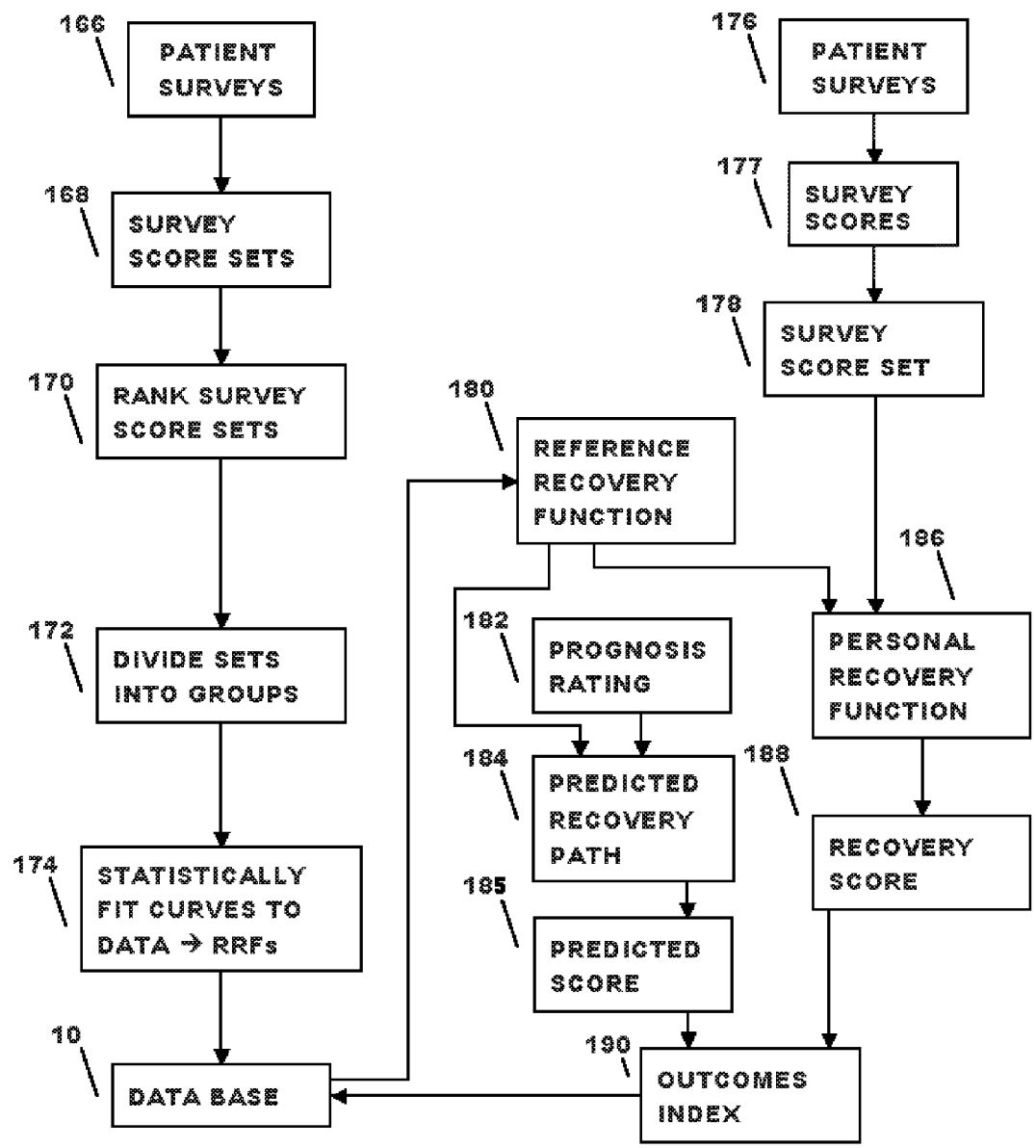
FIG. 10 illustrates a block diagram of an apparatus and method for quantifying patient outcomes in accordance with a preferred embodiment of the present invention.

As an aspect of the present invention, a method is disclosed for comparing a patient's actual recovery score 188 with the patient's predicted recovery score 184, as shown in FIG. 10. This figure shows that initially a number of surveys 166 are utilized to produce a set of reference recovery functions 174, as explained below. These RRFs are then applied to subsequent surveys to obtain a recovery score 188. The foundation of this methodology is a set of surveys 176 that seeks to quantify the progress over time of a patient's health status, preferably as viewed from the patient's own perspective.

When the insured visits a physician or medical treatment provider, a survey 176 is completed. In the preferred embodiment, the survey is self-administered using a data entry device, and, if the patient is being examined by a diagnostic physician, the survey may be presented to the patient by the first processing means 12; if the patient is being treated by a medical treatment provider, it may be presented by the second processing means 14; or, alternatively, it may be presented by some other processing means that may or may not be sited in a provider's office. For example, the input device could be the patient's home computer.

The survey 176 preferably requires that the patient report all signs and symptoms experienced during some recent period and which fall into any of, say, three categories: physical, sensory and functional. We call these changes in health status illness/injury-related effects, or IREs. Physical IREs relate to such factors as scars, acne, amputations and other types of disfigurement. Sensory IREs relate to such sensations as pain, itching, ringing in ears and other symptoms that affect the senses. Finally, functional IREs refer to impairments in the ability of a person to function or perform specific activities with the same proficiency as immediately prior to the onset of the illness or injury. In an alternative embodiment, mental effects, such as apprehension and anxiety, can also be included in the survey.

The purpose of the survey 176 is to identify and characterize each IRE that is related to an illness or injury of the patient. In the preferred embodiment, the patient assigns a value to each IRE that depends on the patient's perception of its severity, say, on a scale of 0 to 10. After the survey is completed, in one embodiment, the diagnostic physician reviews the patient's survey and identifies all of the IREs that appear to be related to the patient's current diagnosis. It is this subgroup of IREs that is used to compute a survey score for the patient. In the preferred embodiment, the database 10 already contains all of the IREs associated with each illness and injury. If the IRE is not in the database with respect to that illness or injury, then it is not scored with respect to the current illness or injury.

For the patient, the ideal outcome is one in which longevity is no less than prior to the onset of the illness or injury, and all of its signs and symptomsd are eliminated immediately. The patient is the best evaluator of these effects; death is an objective fact. Therefore, periodic input from a living patient is all that is required to mechanically compute a survey score 177 from the patient's survey.

The preferred embodiment of the present invention measures the relative reduction or increase in the levels of the IREs over time, weighted by the "concern" that the patient has with each; i.e., it measures the patient's recovery progress as self-determined by the patient. In the preferred embodiment, the weights are obtained as follows: After all of the patient's IREs have been identified and characterized, they are presented to the insured by means of a display device connected to a data entry device. The patient then assigns a weight to each IRE representing the intensity of the patient's desire to eliminate it. For example, the patient could be informed that she can spend a maximum of $100 to eliminate all of the listed IREs. Then she would be asked to indicate the most that she would be willing to spend from her $100 budget to eliminate each one.

It can be inferred that the greater the patient's willingness to spend on a particular IRE, the greater the desire to eliminate it. Based on these weights, a medical treatment provider can assess how best to alleviate the patient's IREs. Moreover, the provider will maximize his own outcomes score 190 by maximizing the patient's future survey scores.

At subsequent visits to a provider with electronic access to the third processing means 16, the patient inputs the current status of his/her IREs, re-scoring the intensity of previously specified IREs and adding and scoring any new ones.

Referring again to FIG. 10, the patient's recovery score 188 is derived from all of the scores from each survey 177 for the current illness or injury; together, these comprise a survey score set 178. Preferably, each IRE, $I_i$, is scored on a ten-point scale: the higher the score, the more intensely does the patient perceive the IRE. The patient's survey score 177 for a survey taken at time t is $$S_t = (10.0 - \Sigma w_i I_{it}) / \Sigma w_i,$$

where $w_i$ ($0 \leq w_i \leq 1$) is the weight that the patient has assigned to the i-th IRE, and I is its intensity. In the preferred embodiment, the weights—assigned during the initial survey—do not change over the course of the patient's recovery. In an alternative embodiment, the patient may supply new weights with each survey.

The weighted sum ($\Sigma w_i I_{it} / \Sigma w_i$) lies between 0 and 10, with higher values associated with more severe signs and symptoms. Since higher prognosis ratings 182 are associated with less signs and severe symptoms, the weighted sum is subtracted from 10.0 to synchronize the survey scores with the prognosis ratings.

Figure 13:
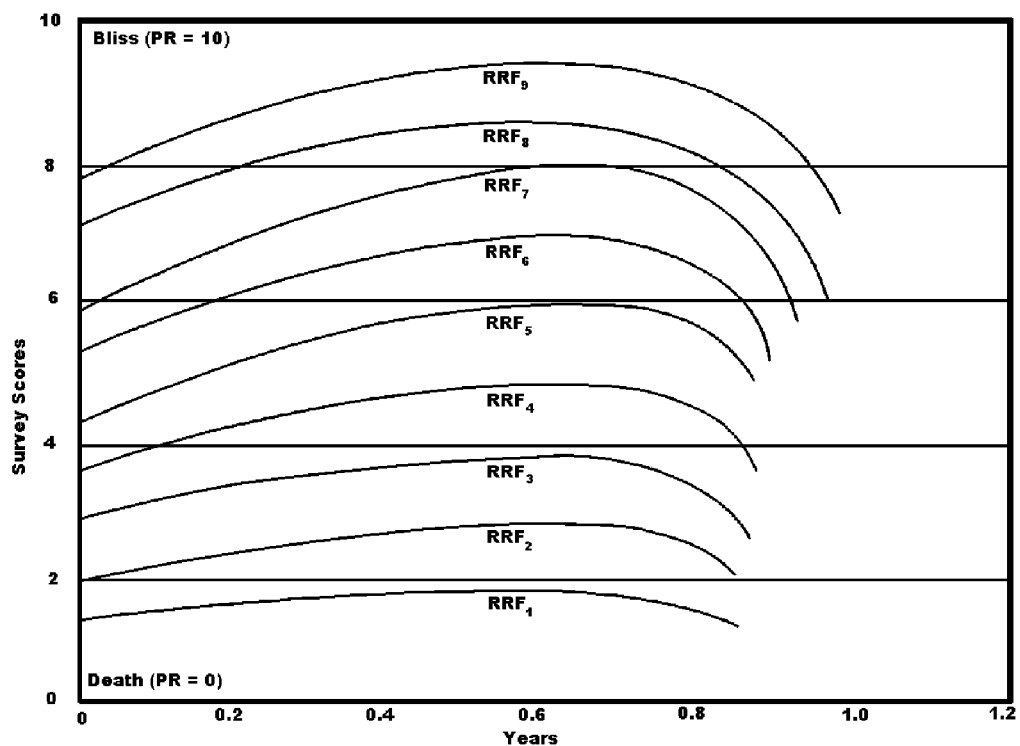
FIG. 13 illustrates a set of reference recovery functions for measuring patient outcomes.

The next step is to develop reference recovery functions (RRFs) 174 and 180; these are the benchmarks against which the patient survey scores are to be compared. In the preferred embodiment, nine RRFs are constructed, which will facilitate ten prognosis rating group[s]. $RRF_P$ (p=0, . . . , 10) is a statistically fitted curve showing the expected recovery path of a patient with a prognosis rating between p and p+1. A set of nine RRFs is shown in FIG. 13. The ordinate axis is an index scale from 0 to 10—it is also the scale for survey scores. $RRF_{10}$ is the horizontal line at the top of the figure; it corresponds to "bliss", a complete absence of IREs. $RRF_0$, the horizontal line at the bottom of the figure, corresponds to death.

Each RRF 174 is derived from a large number of survey score sets 168, a set being defined as all of the survey scores for an individual with respect to a single illness or injury. First, the arithmetic mean or other average statistic of each set of survey scores is computed. These mean scores are preferably sorted in descending order 170 and then preferably divided into approximately nine equal groups 172. Each group 172 consists of a sufficiently large number of survey scores so as to provide statistical significance when the curves are statistically fitted to the data 174. In an alternative embodiment, the survey score sets 168 first are divided into groups according to their prognosis ratings before ranking them. The following treatment is then applied to each sub-group.

In the preferred embodiment, a curve is statistically fitted to the individual survey scores in each group, using a technique such as least squares. In another embodiment, the curve is fitted to the means of the survey score sets 168 comprising each data group. The type of curve that provides the best statistical fit to the data will likely depend on the characteristics of the recovery function for a particular illness or injury. Possible curve types include polynomial functions, elliptical and other conic functions, transcendental functions, as well as linear, linear-logarithmic and mixed functions. All functional types are within the scope of the present invention. An improved fit may also be obtained by estimating with separate functions the different phases of a patient's recovery, such as the "maintenance phase" and the "terminal phase" of a chronic illness.

Once the RRFs are produced, they are added to the database 10 and become available at step 180 for scoring the predicted 184 and actual recovery path (personal recovery function) 186 and recovery score 188. Over time, it is preferred to update the RRFs by using more recent survey score sets 168 to reflect advances in medical techniques and technologies.

The best way to characterize each RRF graphically is by the area under its curve, where the abscissa is measured in years, and the ordinate axis measures the absence of IREs, i.e., the quality of life. This area, when divided by 10 (the upper value of the index), represents "quality-adjusted life-years (QALYs)," [see "Theoretical Foundations of Cost-Effectiveness Analysis," in Cost-Effectiveness in Health and Medicine, Gold, Marthe R. et al., 1996.].

Once the RRFs have been estimated for a given illness, the individual's personal recovery function (RF) 186 is estimated from a set of survey scores 178. The area under the RF, between the first and last survey score in the set, equals the patient's recovery score (RS) 188. Graphically, the personal RF 186 is a curve that goes through each survey score.

To construct the personal RF, first connect each pair of adjacent survey scores by a line segment. Then treat each line segment sequentially. The personal RF will be a curve that lies above, below or on the line segment and its curvature will be based on the curvatures of the RRFs immediately above and below the line segment.

Figure 14:
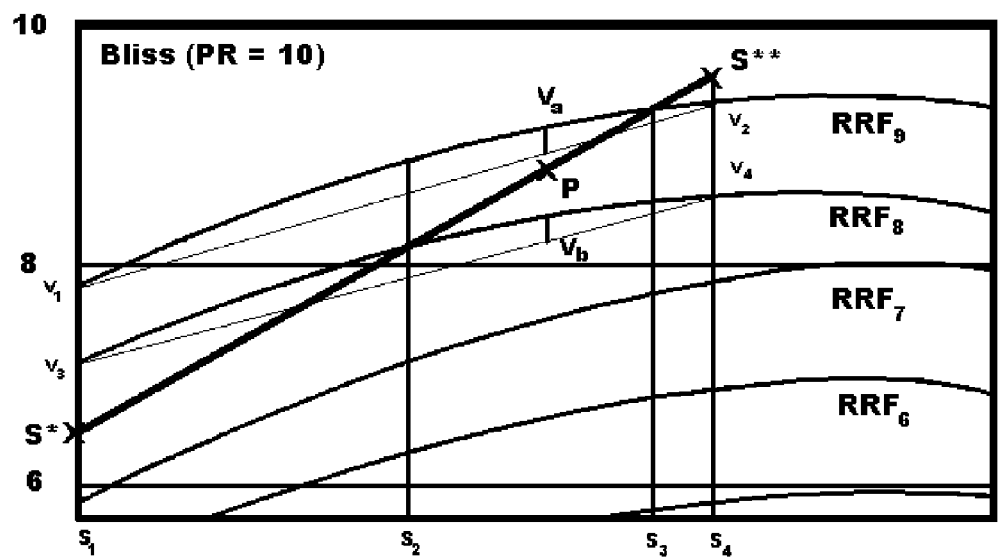
FIG. 14 illustrates a method for estimating the quality-adjusted life-years (QALYs) for a patient recovery function.

FIG. 14, which is an enlarged section of FIG. 13, shows how to construct a recovery function curve between two survey scores, S* and S**, respectively. This curve will lie above the line segment S* S** and will assume the curvature characteristics of the nearby RRFs. First, drop vertical lines from the two survey scores and from each intersection of the survey score line segment with an RRF. In FIG. 14, the four resulting lines intersect the abscissa at $S_1$, $S_2$, $S_3$ and $S_4$. Next, construct a chord between the two points at which the vertical lines at $S_1$ and $S_4$ intersect each of the relevant RRFs. $V_1$ and $V_2$ are the endpoints of the chord for $RRF_9$, and $V_3$ and $V_4$ are the endpoints of the chord for $RRF_8$.

$V_a$ and $V_b$ are the vertical distances between the chords and their corresponding RRFs. Note that $V_a$, $V_b$ and P are aligned on the same vertical, where P is an arbitrary point between $S_2$ and $S_3$. Determine a distance V that is vertically above P, and which is a weighted average of the distances $V_a$ and $V_b$. If P lies between, say, $RRF_8$ and $RRF_9$, then the weights will depend on the distance of the point P from the corresponding chords for $RRF_8$ and $RRF_9$: the closer is P to the chord for $RRF_9$, the larger the weight assigned to $V_a$ relative to $V_b$; and, conversely, the closer P is to the chord for $RRF_8$, the larger the weight assigned to $V_b$ relative to $V_a$.

Similarly, construct a series of other vertical distances between $S_2$ and $S_3$. The locus of points connecting the tops of these distances is one portion of the curve that is constructed above S*S**. Another portion of the curve is constructed between $S_1$ and $S_2$ in the same way, but using the chords for $RRF_7$ and $RRF_8$. Finally, the portion of the arc between $S_3$ and $S_4$ is constructed using the chord for $RRF_9$ and $RRF_{10}$, the "bliss" line. The curves thus constructed between $S_1$ and $S_2$, $S_2$ and $S_3$, and $S_3$ and $S_4$ together comprise the personal RF.

To calculate the recovery score, RS 188, determine the area below the personal RF between $S_1$ and $S_4$, which is easily computed using Simpson's Rule (see any standard calculus text), and then divide by 10. As discussed earlier, this area is in units of QALYs. Call this area $RS_{idp}$, where the subscript refers to the i-th patient, d-th diagnosis, and p-th prognosis rating.

Next, compare the patient's recovery score 188 with the predicted score 185 based on the patient's prognosis rating 182. As before, compute the area under a curve between $S_1$ and $S_4$ using Simpson's Rule, but this time for the RRF associated with the patient's prognosis rating. If the patient's prognosis rating 182 contains a fractional part, such as 7.2, then the predicted score is interpolated from the RRFs that bracket the prognosis rating, i.e., $RRF_7$ and $RRF_8$. First, compute $A_7$ and $A_8$, the areas under $RRF_7$ and $RRF_8$, respectively. Then the predicted score, PS, in QALYs is $$PS = A_7 + (PR - \text{int}(PR))(A_8 - A_7)/10,$$

where int(PR) is the integer value of the prognosis rating. In the example, int(7.2)=7.

There are several ways to combine the recovery scores of patients to obtain an outcomes measure 190 for a provider. One measure is $$M_{dp}^* = (\Sigma_i RS_{idp}/\Sigma_i \text{years}_i)/I,$$

where $\Sigma_i \text{years}_i$ is the total number of actual years over which the recovery scores are measured and I is the total number of patients being scored. Note that the best possible score for M* is 1.0 and occurs only if a doctor has eliminated all of the IREs of all of the patients in this group instantly and completely and has fully restored their longevity. The closer is M* to 1.0, the closer is the doctor to perfection.

Another measure is $$M_{dp}^{+} = (\Sigma_i (RS_{idp}/PS_{idp}))/I.$$

This is the sum of the ratios of actual patients scores to their predicted scores. A value of 1.0 indicates that the doctor, on average, just meets expectations, while a higher (lower) value indicates that he exceeds (falls short of) expectations.

A third measure is $M_{dp}^{\#} = \Sigma_i RS_{idp}/\Sigma_i PS_{idp}$.

A fourth embodiment is to estimate statistically the following relationship, using all doctors' patients, i, having a diagnosis d and prognosis rating in group p:

$$Y_{idp} = b_0 + b_1 M_{idp}^* + b_2 M_{idp}^{+} + b_3 PR_{idp} + b_4 \ln Q_{idp} + u, \text{ where } Y_{idp} \text{ is the actual outcome in QALYs,}$$

$M_{idp}^*$ and $M_{idp}^{\#}$ are as defined above, $PR_{idp}$ is the prognosis rating, $\ln Q_{idp}$ is the natural logarithm of the number of times the doctor has performed the treatment, $b_0, \ldots, b_4$ are parameters to be estimated, and u is a randomly distributed error term.

Once this relationship is estimated, then $Y_{idp}$ is computed for each doctor with respect to his i patients in the dp-th category, using the estimated parameter values. Finally, the arithmetic mean of the $Y_{idp}$ is computed for each doctor, which becomes that doctor's Outcomes Index.

An empirical analysis can be applied to determine which of the above or other measures of the Outcomes Index is preferred. The selection of the preferred measure would therefore be empirically determined and applied. The preferred measure can vary by illness or by other factors.

It is preferred that the Outcomes Index remains a dynamic measure, because improvements in outcomes will evolve with medical practice and technology. Therefore, it is preferred that the RRFs be re-estimated from time to time with more recent survey score sets.

This raises the question of whether previously computed RSs and RFs are to be recomputed each time the RRFs are updated. It is preferred that, in order to maintain stability in the Outcomes Index, only the latest survey scores are computed using the latest RRFs. Thus, an Outcomes Index may be based on recovery scores that are themselves based on different vintages of the RRFs.

The Effect of Co-Morbidities

Co-morbidities present a special problem in that two or more diagnostic codes may be involved, and two or more providers may have lead responsibilities. The effects of each disease and the responsibilities for the patient's recovery must be disentangled.

Several embodiments to the co-morbidity problem are presented within the scope of the present invention. The simplest embodiment is not to address the co-morbidities explicitly. This means the RRFs 180, and therefore the Outcomes Index 190, may include multiple diagnoses. For example, the RRFs produced for Chagas heart disease (ICD-9 0860) might include the effects of the same patient's melanoma (as a co-morbidity). In this example, the Outcomes Index of the doctor treating the patient's melanoma would be affected by the performance of the doctor treating the Chagas heart disease, and vice versa. A further disadvantage is that this solution would likely increase the variance of the survey score sets 178 that comprise the RRFs 180, which would in turn make the Outcomes Index 190 a less-precise measure of a provider's performance.

A second embodiment excludes all cases involving significant co-morbidities. For example, if a patient has both colon cancer and diabetes, that patient's survey scores for these diseases are excluded entirely. A disadvantage with this approach is that doctors would know that they are not being evaluated for patients with serious co-morbidities and might be less conscientious as a result. There is also the perverse incentive for the provider, whose treatment of a patient is not going well, to "find" some co-morbidity for the patient so that the patient's recovery score will not count in his Outcomes Index.

A better embodiment is to adjust the original prognosis rating 182 whenever the patient contracts a new illness, provided that the new illness is not a complication of an existing illness. In this case, the diagnostic physician assigns a prognosis rating 182 to the new illness, taking into consideration the likely effect of the original illness on the patient's recovery. A diagnostic physician also assigns a new prognosis rating to the original illness, given that the new illness will likely also affect the patient's recovery. All subsequent additions to the provider's Outcomes Index 190 are based on these new prognosis ratings. Under this embodiment, the RRFs 174 themselves should exclude all survey score sets involving significant co-morbidities. This embodiment has the advantage that estimates of the RRFs will usually have a smaller variance than if co-morbidities are included in the data set.

Another embodiment applies a comprehensive econometric model that measures the effects of illness and injury, including co-morbidities, on remaining life years. It is preferred that the model be estimated with data on patients who have already gone through their life span, including patients who have died from natural causes.

Consider the relationship $$Y = a_0 + a_1 A + b_1 D_1 + \ldots + b_n D_n + c_1 P_1 + \ldots + c_n P_n + d_1 D_1 D_2 + d_2 D_1 D_3 + \ldots + u,$$

where

A is the age of the patient, $P_d$ is the prognosis rating for illness d (d=1, ..., n); $P_d = 0$ if the illness is not present, $P_d$ is a dummy variable with a value of 1 if the illness d is present, 0 if it is not present, $D_d D_{d'}$ is a term for the interaction between illness d and illness d', Y is the time between the patient's original diagnosis and the time of death, $a_0, a_1, b_1, \ldots, b_n, c_1, \ldots, c_n, d_1, \ldots, d_n,$ are parameters to be estimated, and u is a randomly distributed error term.

The model states that the value of Y depends on the age of the patient, the illnesses that the patient has been diagnosed with, and the patient's prognosis ratings for those illnesses. For some illnesses, the gender and/or ethnicity of the patient are also relevant.

The dummy variables $P_d$ (d=1, ..., n) exclude from the model illness(es) that are not currently present, but they also serve to distinguish between the case where an illness is present and the prognosis rating is 0.0 (D=1; P=0.0) from the case where the d-th illness is not present (D=0; P=0.0).

The interaction term, $D_d D_{d'}$, is designed to measure any effects that are in addition to the individual effects of the two illnesses. In other embodiments, the model can include terms such as $D_d D_{d'} D_{d''}$ to measure the additional effects due to tri-morbidities, etc.

This econometric model provides an estimate of the effect of different illnesses and injuries, as well as co-morbidities, on expected remaining life. In another embodiment, the model is extended by adding a time dimension that estimates the effects of varying time intervals between the onsets of the co-morbidities.

In yet another embodiment, the model is estimated with the Outcomes Index of the treating doctor as an independent variable and expected remaining life as the dependent variable. This model can be used to predict the effect on expected remaining life of treatment by doctors with different Outcomes Indexes.

In Case of Death

When a person dies, quality-adjusted life is assumed to fall to zero. This can have a substantial impact on a doctor's Outcomes Index 190, so it is important to measure this effect as accurately as possible. This raises two related issues: 1) if a patient dies prematurely, how do we penalize the doctor's Outcomes Index if it is unclear to what extent the death is related to the diagnosis that the doctor was treating; and 2) how long after the patient's treatment and to what extent should a doctor be penalized for the patient's death?

In one embodiment, a "statute of limitations" can be applied to the patient's recovery score. For example, if a patient dies more than five years after the initial diagnosis, we could assume that the patient's death is due to other causes, and/or we could weight the impact on the recovery score by the likelihood that the disease in question is the primary cause of the patient's death, declining from, say, 100% in the first year to 20% in the fifth year.

In another embodiment, the econometric model described above is estimated. Compute Y for a single patient, using estimated values for the parameters. If the patient dies in less than Y years, then future QALYs are lost, where future QALYs are equal to the area under the predicted RRF between the time of death and the time at which the predicted RRF crosses the death line (abscissa). In another embodiment, the cause-of-death entry on the patient's death certificate could be used. The problem here is that it is the treating provider who fills out the death certificate, and he has an incentive to enter a cause of death that has the most favorable impact on his Outcomes Index 190.

Figure 15:
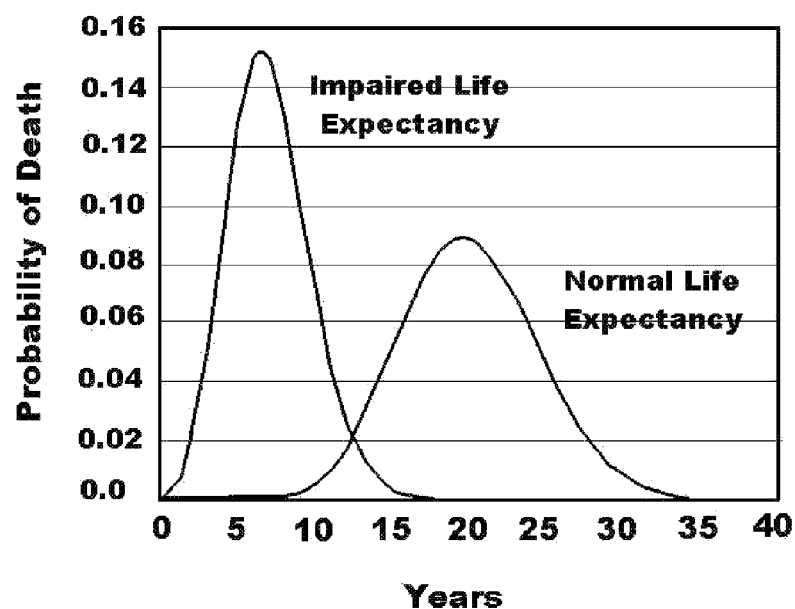
FIG. 15 illustrates probability distributions for the remaining life of a healthy 55-year-old male and an impaired 55-year-old male.

The preferred embodiment uses statistical methods to estimate the probability distributions shown in FIG. 15. The example distribution on the left shows the probability of death as a function of time based on a diagnosis for a 55-year-old male with a specific illness and prognosis rating. The probability of death is equal to the area under the curve between two time periods. The probability distribution on the right shows the probability of death, but for a 55-year-old male with no disease present. Technically, this distribution should represent a person with no disease present, and who does not die from the disease in question.

In this example the two curves cross at about 12 years from the time of the initial diagnosis; thus, if the person dies at twelve years, it is equally likely that death is due to the illness as from some other cause. In this case, half of the loss of future QALYs can be attributed to the illness, where future QALYs are measured as above.

The loss of QALYs due to death at other times can be estimated as follows. Let $y=f(t)$ and $z=g(t)$ be the respective probability distributions for normal and for impaired life expectancy, and $F(t)$ and $G(t)$ be the corresponding cumulative probability distributions. Let $t_d$ be the time of death, where time is measured as the number of years following the initial diagnosis. Then the appropriate weight to apply to the loss of future QALYs is $(1-G(t_d))/(2-F(t_d)-G(t_d))$. One skilled in the art will be able to specify the correct weight for other probability distributions.

In some applications, it is preferred to discount future QALYs.

Two other aspects of the current invention further promote health care quality. The first consists of a method for assessing the accuracy and timeliness of a physician's diagnoses. In the preferred embodiment of the present invention, the diagnostic physician can enter up to three diagnostic codes (see step 26 at FIG. 4) prior to preparing a treatment plan. The first code is the primary diagnostic code. The purpose of including multiple diagnostic codes in the treatment plan is to convey to the treatment provider any uncertainty that the diagnostic physician has in establishing the correct diagnosis. For each diagnostic code entered, the physician also enters his estimate of the probability that the diagnostic code accurately describes the patient's illness.

The Diagnostic Accuracy Index (DAI) is constructed from the diagnostic codes and their associated probabilities. In the preferred embodiment, the codes can be altered without penalty until a treatment provider has performed a non-emergency treatment in accordance with the patient's treatment plan. At that point in time, the diagnoses and their probabilities are considered "fixed" for the purpose of computing the DAI.

The accuracy score for a given treatment plan is $$AS = (S_1 * Prob_1 + S_2 * Prob_2 + S_3 * Prob_3)/D,$$

where $S_i$ equals +1 if the diagnosis is true and $S_i$ equals $r$ if it is not, where $-1 < r < 0$. The purpose of the constant $r$ is to provide an incentive for including diagnoses that have some likelihood of being true rather than omitting them. It serves to diminish the penalty if the diagnosis is included but is not correct, compared with the penalty for omitting it entirely. The value for $r$ determines the severity of the penalty.

The term D is designed to impose a time penalty for establishing a correct diagnosis after a certain amount of time has elapsed. The term D can assume different forms; the only requirement is that the penalty increases with time, after a no-penalty period. For example, let $D=(W+1)-F$ for $W>F$; $D=1$ otherwise. W is the length of time taken to establish a correct diagnosis, and F is an initial period during which the penalty is zero.

Another acceptable functional form for D is $D=a-(b/W)$ for $W>b/a=F$; $D=1$ otherwise. The maximum penalty occurs at $a$, $0 \leq a \leq 1$. D approaches the maximum penalty asymptotically as W increases. The penalty remains at zero ($D=1$) during the no-penalty period. In both examples, the rate at which the penalty increases can be hastened or retarded by decreasing or increasing the number of days per unit W.

The diagnostic physician's accuracy score, DAI, is preferably computed as the arithmetic mean of the individual accuracy scores:

$$DAI = 100(\Sigma AS_j)/N, \text{ where } AS_j \text{ is the } j\text{-th accuracy score and } N \text{ is the number of accuracy scores.}$$

Once the diagnoses are fixed, a subsequent_change in the patient's primary diagnosis will result in a new treatment plan with a new set of diagnoses and probabilities. If the probabilities change, but the primary diagnosis does not, no new treatment plan is created.

Another device in accordance with the present invention quantifies the complication rate of a medical treatment provider, especially a surgeon. The Complications Index (CI) operates similarly to the DAI. The lead treatment provider is designated by the diagnostic physician. At the patient's first visit, the lead provider designates up to three possible complications and their corresponding probabilities. If a complication does occur, it is weighted by 1 minus its probability, and then one-half of its probability is added to the score: Complication Score $= \Sigma (S_i(1-Pr_i)+0.5*Pr_i)$, where $S_i=+1$ if the complication occurs and 0 if it does not; and $Pr_i$ is the occurrence probability assigned to the i-th complication.

What this formula does is mitigate the complication score to the extent that the complication has been correctly predicted. However, if the complication occurs, the score is increased. The CI is the average of all complications scores; i.e., the scores for all of the provider's patients with a specific illness and a specific prognosis rating. The complications rate is expected to increase as the prognosis rating decreases, ceteris paribus. The complication score is minimized, first by avoiding complications, but secondly by correctly predicting complications. Accurate prediction of the complications rate provides useful information to the patient prior to selecting a provider.

In one embodiment of providing comparative information about treatment providers, FIG. 16 provides an example using an Outcomes Index. The Outcomes Index described herein is used to enable, for instance, a patient to compare for the patient's specific diagnosis and prognosis rating, outcomes measures for potential treatment providers, such as physicians and hospitals. The Doctor Shopper.sup.SM report, as shown in FIG. 16 and developed by the inventor, as an example of the use of, for instance, the Outcomes Index—which is one aspect of the present invention—clearly demonstrates how patients and health care providers may beneficially use the Outcomes Index. Based on self-administered survey data in a database and by automatically processing data in the database, one may generate comparative reports that may include an Outcomes Index.

A comparative report that is provided as an aspect of the present invention may use tables, text, graphs or other textual and graphical means to reflect an Outcomes Index. A comparative report may be used by an insured for selecting a treatment provider and/or hospital. A comparative report may also be used by insurers for ratings of care providers such as physicians and hospitals. A comparative report may also be used by hospitals to rate their own performance and to take measures for performance improvements. A comparative report may be used by an insured for selecting an insurer and its health care network. It may also be used for any other provider that affects the outcome of a treatment of a patient. Accordingly a comparative report that may include an Outcomes Index is a decision support document.

A comparative report may also comprise information about care providers, including information of years in practice, name of attended medical school, medical school ranking, academic ranking of the medical school, number of malpractice suits a provider was involved in, and any other information related to a care provider. This aspect, as part of a comparative report, is shown in an illustrative example in FIG. 17. This aspect of a comparative report of care providers as shown in FIG. 17 may be called "credentials".

A method here provided as an aspect of the present invention can be performed by a processor that is part of a system. The steps of a method can be stored as instructions in a memory that can be accessed by the processor. A processor may be a distributed processor that may include more than one individual processor and may reside in different physical locations. It may also reside in a single computer device. A processor may act upon data that is retrieved from a database, and it may store results in a database. A database may comprise different storage locations as different individual databases. Databases and processors may be connected to a network. Work stations, such as personal computers, may be used to communicate with a processor and/or a database. Data may be retrieved through the network or provided to a database or a processor through the network. The network may be a private network. It may also be a public network, such as the Internet. On-line in the context of the present invention means communicating with a processor or database, possibly through a workstation or any other computing or communication device including a wireless device, wherein a device is connected to the processor and/or database through a network including the Internet.

The following reference is generally descriptive of the background of the present invention and is hereby incorporated herein by reference: Cost-Effectiveness in Health and Medicine, Gold, Marthe R., Louise B. Russell, Joanna E. Siegel, Milton C. Weinstein. Oxford University Press, New York. 1996.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

The invention claimed is:

1. A system for automatically administering a health plan, comprising:
    a. a processor; and a memory in communications with said processor, the memory including program code executable by said processor providing primary data for a first database, and processing said primary data automatically into a second database, whereby said second database comprises processed data;
    b. an automated health plan administrator, comprising:
        i. said first database comprising primary data originating from: enrollment and disenrollment of insured patients and dependents, enrollment and disenrollment of diagnostic physicians, enrollment and disenrollment of providers, including medical treatment providers; self-administered surveys by insured patients; insurers providing insurance coverage information; vendors providing diagnostic codes and their descriptions for each of a plurality of diagnoses; and vendors providing procedure and medical equipment codes and their description for each of a plurality of procedures and medical equipment; and processing said primary data automatically into processed data;
        ii. said second database comprising processed data: enrollment data of insured patients, diagnostic physicians, and other providers, including medical treatment providers and; a benefit payable in the event a procedure is prescribed and provided; a list of medical providers available for providing said procedure, and each provider's charge for providing said procedure; and historical data, by said diagnostic code, comprising patient outcomes ratings that indicate a prognosis rating versus an outcomes index that is based on the recoveries of prior patients and is measured in quality-adjusted life-years, whereby the improvement consists of measuring patient outcomes in terms of quality-adjusted life-years;
        iii. first processing means: for producing for an insured patient a treatment plan that specifies the identity of said insured, at least one procedure to be provided, and a prognosis rating;
        iv. second processing means for producing a treatment record that specifies at least one procedure actually provided to said insured patient and the actual charge for providing each said procedure; and where each said procedure is selected from only one of the group: original treatment plan; treatment plan including at least one alternative procedure, and for which the total benefit payable for all said procedures provided in said treatment plan does not exceed the total benefit payable for said original treatment plan;
        v. third processing means for processing said treatment plan and said treatment record to determine an amount payable to said medical treatment provider, equaling the lesser of the amount charged for procedures provided and the benefit payable for procedures provided; and determining an amount payable to the policyholder of said insured's policy, equaling the amount by which the benefit payable for all said procedures provided less the actual charges for providing said procedures exceeds zero;
    c. calculating at least one recovery score for said insured patient and adjusting said outcomes index of said medical treatment provider to include said recovery score of said insured patient; and
    d. accessing said second database to add said insured patient's said prognosis rating and said recovery score, and said medical treatment provider's said adjusted outcomes index, wherein the improvement comprises the capability of comparing the outcomes index of one medical treatment provider with the outcomes index of other medical treatment providers with respect to a given diagnosis and for patients with comparable prognosis ratings.

2. The system as claimed in claim 1, further including a schedule of benefits that is automatically constructed, comprising the following steps: for medical treatment providers providing services within a predetermined geographic area, the amounts charged to provide a given procedure are ranked in descending order by said third processing means; the highest price charged among the bottom X percent of said amounts charged is established as the benefit payable for said procedure; and the benefit level for said procedure is defined as X percent and is stored in said first database, wherein the improvement comprises said third processing means applying a predetermined benefit level to a plurality of covered procedures to determine a schedule of benefits for said covered procedures.

3. The system as claimed in claim 1, wherein said amounts charged by said medical treatment providers are automatically extracted from medical claims during processing by said third processing means and stored in said second database; further providing that amounts charged can be entered by data entry means into said second processing means, stored in said first database and processed by said third processing means into said second database.

4. The system as claimed in claim 1, further including an automatically generated comparative report for the benefit of said insured patient, comprising:
   a. said procedures that are listed in said treatment plan and the benefit payable for each said procedure;
   b. a plurality of medical treatment providers offering said procedures, the outcomes index of each said medical treatment provider with respect to said diagnosis and said prognosis rating of said insured patient, and the amount each said medical treatment provider charges to provide each said procedure;
   c. a value chart depicting for said medical treatment providers the relationship between said outcomes index and the total amount charged for the set of services selected from the following group: the set of all said procedures in said treatment plan, and the set of all procedures to be provided including at least one said alternative procedure; and
   d. credentials and selected personal characteristics of said medical treatment providers, whereby said insured patient can receive said comparative report to compare listed treatment options after receiving said treatment plan, but prior to selecting a medical treatment provider for treatment.

5. The system as claimed in claim 1, further including an automated process for confirming in real time the eligibility of a patient to receive covered benefits under said health plan, comprising a means for paying a premium on-line and a means for confirming that said premium has been paid, comprising a record of said premium payment residing in said second database, whereby said first and said second processing means can access said second database to confirm said payment of said premium and therefore eligibility of said patient.

6. The system as claimed in claim 1, further including the automated maintenance of an electronic medical record, comprising: processing changes of primary data in said first database, and automatically reprocessing said primary data and storing said processed data in said second database; automatically reprocessing said processed data within said second database; and further including an automated process for updating said first and second databases as a result of changes in: covered benefits, enrollment, treatment plans, treatment records, procedures provided by providers, prices, medical procedures, self-administered surveys, patient outcomes and other performance measures for medical treatment providers, performance measures for diagnostic physicians, and other medical transactions.

7. The system as claimed in claim 1, further including in said first database a pairing of diagnoses with illness- and injury-related signs and symptoms, wherein said signs and symptoms that are causally related to each said diagnosis can be determined automatically.

8. The system as claimed in claim 1, further including an automated process for providing billing and claim processing information to said second database, and billing said insured patients, comprising accessing said second database, identifying said insured patients with outstanding balances due to medical treatment providers, and processing said billing and said claim processing information into processed data, whereby said insured patients can be notified regarding amounts due.

9. The system as claimed in claim 1, further including an automated process for reconciling the monetary accounts of the insurer, providers and insureds, comprising accessing said second database to further process debits and credits relating to: insurance coverage information, including benefits payable, deductibles, co-pays; health savings account transactions; and balances due to providers, insurers and insureds.

10. The system as claimed in claim 1, further including an automated process for evaluating health care records to detect fraud, comprising: selecting related treatment plans and treatment records from the group: patient's magnetic medium, first processing means, second processing means, second database and third processing means; comparing said related treatment plans and treatment records for consistency; and flagging inconsistent records for further investigation.

11. The system as claimed in claim 1, further including an automated process for updating said first and said second databases, comprising changes in: covered benefits, enrollment, treatment plans, treatment records, master files, procedures provided by providers, amounts charged, new medical procedures, self-administered surveys, patient outcomes and other performance measures for medical treatment providers, performance measures for diagnostic physicians, and other medical data used by said system.

12. The system as claimed in claim 1, comprising automated processes for: enrolling and disenrolling members on-line; enrolling and disenrolling diagnostic physicians on-line; enrolling and disenrolling medical treatment providers and other providers on-line; producing insurance information on-line; processing treatment plans; processing treatment records; processing health plan benefits; producing comparative reports; producing schedules of benefits; producing real-time confirmation that a patient is eligible to receive covered benefits; maintaining a system of electronic medical records; disbursing funds to insurers, insureds, medical treatment providers and other providers; billing insureds for amounts due to medical treatment providers and other providers; reconciling monetary accounts of insurers, providers and insureds; and updating said first and said second databases to reflect additions, deletions and revisions, and processing said additions, deletions and revisions within said second database, whereby the improvement consists of automating and integrating all essential processes that are required to administer a health plan in a fully automated mode.

13. The system as claimed in claim 1, further comprising: a set of Reference Recovery Functions (RRFs) produced from historical patient data; generating a predicted recovery score for a patient using the said set of RRFs; computing an actual recovery score for said patient using a set of the patient's data with the said set of RRFs; and calculating an outcomes index by using said predicted recovery scores with said actual recovery scores for a plurality of patients with comparable prognosis ratings.

14. The system as claimed in claim 1, the system further enabled to include an automated process for maintaining an archive of editable treatment plan prototypes, comprising prior treatment plans from which identifying information has been excluded, and which may be used in whole or in part to produce a new treatment plan, whereby the time and effort required to produce a new treatment plan is reduced.

15. The system as claimed in claim 1, comprising providing an automated process for evaluating quantitatively a diagnostic accuracy index for a diagnostic physician, including for each treatment plan the steps: assigning at least one diagnostic code to a patient; assigning a probability that each said diagnostic code predicts the likelihood that said diagnostic code corresponds to the episode of illness or injury of said patient; determining an accuracy score based on said diagnostic codes, said probabilities, said patient's final diagnosis, and elapsed time between said patient's initial office visit for said treatment plan and assignment of said final diagnosis; and computing for each said diagnostic physician a diagnostic accuracy index based on said accuracy scores produced over a predetermined recent period, whereby said diagnostic physicians' diagnoses are rated with respect to predictive accuracy and timeliness, and can be compared with said diagnostic accuracy indices of other diagnostic physicians.

16. The system as claimed in claim 1, the system further enabled to perform automatically producing a complications index for a medical treatment provider, including the steps: assigning to a treatment plan at least one possible complication that could occur during the administering of said treatment plan; assigning a probability that each said complication will occur during administering said treatment plan; determining a complication score based on the actual occurrence of said complications and their respective said probabilities; and computing for each said medical treatment provider a complications index based on said complication scores produced over a predetermined recent period, whereby said medical treatment providers' complications are rated with respect to frequency, severity and predictive accuracy and can be compared with said complication indices of other medical treatment providers.

17. The system as claimed in claim 1, the system further enabled to perform automatically the steps of providing an automated just-in-time appointment scheduler for a medical service provider, comprising a processing means that: stores the current day's schedule of appointments; stores the sign-in time of each patient; stores the time at which said medical service provider starts reviewing the electronic medical records of each scheduled patient; and, when queried by a scheduled patient by means of a communications device, said processing means computes and reports to said scheduled patient an updated appointment time for said patient.

18. The method as claimed in claim 1, providing in said first database the pairing of diagnoses with illness- and injury-related signs and symptoms, wherein said signs and symptoms that are causally related to each said diagnosis can be determined automatically.

19. A method for automatically administering a health plan, comprising:
  a. providing primary data to a first database originating from: enrollment and disenrollment of insured patients and dependents, enrollment and disenrollment of diagnostic physicians, enrollment and disenrollment of providers, including medical treatment providers; self-administered surveys by insured patients; from insurers providing insurance coverage information; vendors providing diagnostic codes and their descriptions for each of a plurality of diagnoses; and vendors providing procedure and medical equipment codes and their description for each of a plurality of procedures and medical equipment; and processing said primary data automatically into processed data;
  b. providing processed data to a second database, comprising: enrollment data of insured patients, diagnostic physicians, and medical treatment providers and other providers; a benefit payable in the event a procedure is prescribed and provided; a list of medical treatment providers available for providing said procedure and each provider's charge for providing said procedure; and historical data, by said diagnostic code, comprising patient outcomes ratings that indicate a prognosis rating versus an outcomes index that is based on the recoveries of prior patients and is measured in quality-adjusted life-years, whereby the improvement consists of measuring patient outcomes in terms of quality-adjusted life-years;
  c. providing a first processing means, comprising: producing for an insured patient a treatment plan that specifies the identity of said insured, at least one procedure to be provided, a prognosis rating and said benefit payable;
  d. providing a second processing means, comprising: producing a treatment record that specifies at least one procedure actually provided to said insured patient and the actual charge for providing each said procedure; and where each said procedure is selected from the group: original treatment plan; treatment plan including at least one alternative procedure, and for which the total benefit payable for all said procedures provided in said treatment plan does not exceed the total benefit payable for said original treatment plan;
  e. providing a third processing means, comprising: processing said treatment plan and said treatment record to determine an amount payable to said medical treatment provider, equaling the lesser of the amount charged for procedures provided and the benefit payable for each said procedure provided; and determining an amount payable to the policyholder of said insured's policy, equaling the amount by which the benefit payable for all said procedures provided less the actual charges for providing said procedures exceeds zero.

20. The method as claimed in claim 19, providing automatically generating a schedule of benefits, comprising the following steps: for medical treatment providers providing services within a predetermined geographic area, the amounts charged to provide a given procedure are ranked in descending order by said third processing means; the highest price charged among the bottom X percent of said amounts charged is established as the benefit payable for said procedure; and the benefit level for said procedure is defined as X percent and is stored in said first database, wherein the improvement comprises said third processing means applying a predetermined benefit level to a plurality of covered procedures to determine a schedule of benefits for said covered procedures.

21. The method as claimed in claim 19, comprising providing amounts charged by said medical treatment providers that are automatically extracted from medical claims during processing by said third processing means and stored in said second database; further providing that amounts charged can be entered by data entry means into said second processing means, stored in said first database and processed by said third processing means into said second database.

22. The method as claimed in claim 19, providing an automatically generated comparative report for the benefit of said insured patient, comprising:
   a. listing said procedures that are in said treatment plan and the benefit payable for each said procedure;
   b. listing a plurality of medical treatment providers offering said procedures, the outcomes index of each said medical treatment provider with respect to said diagnosis and said prognosis rating of said insured patient, and the amount each said medical treatment provider charges to provide each said procedure;
   c. presenting a value chart depicting for said medical treatment providers the relationship between said outcomes index and the total amount charged for the set of services selected from the following group: the set of all said procedures in said treatment plan, and the set of all procedures to be provided including at least one said alternative procedure; and
   d. listing said credentials and selected personal characteristics of said medical treatment providers,
whereby said insured patient can receive said comparative report to compare listed treatment options after receiving said treatment plan, but prior to selecting a medical treatment provider for treatment.

23. The method as claimed in claim 19, providing an automated process for confirming in real time the eligibility of a patient to receive covered benefits under said health plan, comprising a means for paying a premium on-line and a means for confirming that said premium has been paid, comprising a record of said premium payment residing in said second database, whereby said first and said second processing means can access said second database to confirm said payment of said premium and therefore eligibility of said patient.

24. The method as claimed in claim 19, providing an automated process for maintaining an electronic medical record, comprising: processing changes of primary data in said first database, automatically reprocessing said primary data and storing said processed data in said second database; and automatically reprocessing said processed data within said second database; and further providing an automated process for updating said first and second databases as a result of changes in: covered benefits, enrollment, treatment plans, treatment records, procedures provided by providers, prices, medical procedures, self-administered surveys, patient outcomes and other performance measures for medical treatment providers, performance measures for diagnostic physicians, and other medical transactions.

25. The method as claimed in claim 19, providing an automated process for providing billing and claim processing information to said second database, and billing said insured patients, comprising accessing said second database, identifying said insured patients with outstanding balances due to medical treatment providers, and processing said billing and said claim processing information into processed data, whereby said insured patients can be notified regarding amounts due.

26. The method as claimed in claim 19, providing an automated process for reconciling the monetary accounts of the insurer, providers and insureds, comprising accessing said second database to further process debits and credits relating to: insurance coverage information, including benefits payable, deductibles, co-pays, health savings account transactions and balances due to providers, insurers and insureds.

27. The method as claimed in claim 19, further providing an automated process for evaluating health care records to detect fraud, comprising: selecting related treatment plans and treatment records from the group: patient's magnetic medium, first processing means, second processing means, second database and third processing means; comparing said related treatment plans and treatment records for consistency; and flagging inconsistent records for further investigation.

28. The method as claimed in claim 19, further providing an automated process for updating said first and said second databases, comprising changes in: covered benefits, enrollment, treatment plans, treatment records, master files, procedures provided by providers, amounts charged, new medical procedures, self-administered surveys, patient outcomes and other performance measures for medical treatment providers, performance measures for diagnostic physicians, and other medical data used by said system.

29. The method as claimed in claim 19, comprising providing automated processes for: enrolling and disenrolling members on-line; enrolling and disenrolling diagnostic physicians on-line; enrolling and disenrolling medical treatment providers on-line; producing insurance information on-line; processing treatment plans; processing treatment records; processing health plan benefits; producing comparative reports; producing schedules of benefits; producing real-time confirmation that a patient is eligible to receive covered benefits; maintaining a system of electronic medical records; disbursing funds to insureds, medical treatment providers and other providers; billing insureds for amounts due to medical treatment providers and other providers; reconciling monetary accounts of insurers, providers and insureds; and updating said first and said second databases to reflect additions, deletions and revisions, and processing said additions, deletions and revisions within said second database, whereby the improvement consists of automating and integrating all essential processes that are required to administer a health plan in a fully automated mode.

30. The method as claimed in claim 19, further comprising: creating a set of Reference Recovery Functions (RRFs) from historical patient data; generating a predicted recovery score for a patient using the said set of RRFs; generating an actual recovery score for said patient using a set of the patient's data with the said set of RRFs; and calculating an outcomes index by using said predicted recovery scores with said actual recovery scores for a plurality of patients with comparable prognosis ratings.

31. The method as claimed in claim 19, comprising providing an automated process for maintaining an archive of editable treatment plan prototypes, comprising prior treatment plans from which identifying information has been excluded; and which may be used in whole or in part to produce a new treatment plan, whereby the time and effort required to produce a new treatment plan is reduced.

32. The method as claimed in claim 19, comprising providing an automated process for evaluating quantitatively a diagnostic accuracy index for a diagnostic physician, including for each treatment plan the steps: assigning at least one diagnostic code to a patient;
   assigning a probability that each said diagnostic code predicts the likelihood that said diagnostic code corresponds to the episode of illness or injury of said patient; determining an accuracy score based on said diagnostic codes, said probabilities, said patient's final diagnosis, and elapsed time between said patient's initial office visit for said treatment plan and assignment of said final diagnosis; and computing for each said diagnostic physician a diagnostic accuracy index based on said accuracy scores produced over a predetermined recent period, whereby said diagnostic physicians' diagnoses are rated with respect to predictive accuracy and timeliness, and can be compared with said diagnostic accuracy indices of other diagnostic physicians.

33. The method as claimed in claim 19, comprising providing an automated process for producing a complications index for a medical treatment provider, including the steps: assigning to a treatment plan at least one possible complication that could occur during the administering of said treatment plan; assigning a probability that each said complication will occur during administering said treatment plan; determining a complication score based on the actual occurrence of said complications and their respective said probabilities; and computing for each said medical treatment provider a complications index based on said complication scores produced over a predetermined recent period, whereby said medical treatment providers' complications are rated with respect to frequency, severity and predictive accuracy and can be compared with said complication indices of other medical treatment providers.

34. The method as claimed in claim 19, comprising providing an automated just-in-time appointment scheduler for a medical service provider, comprising a processing means that: stores the current day's schedule of appointments; stores the sign-in time of each patient; stores the time at which said medical service provider starts reviewing the electronic medical records of each scheduled patient; and, when queried by a scheduled patient by means of a communications device, said processing means computes and reports to said scheduled patient an updated appointment time for said patient.

* * * * *